United States Patent
Wallace

(10) Patent No.: US 7,056,931 B2
(45) Date of Patent: Jun. 6, 2006

(54) 2-SUBSTITUTED 1,2,3,4-TETRAHYDROQUINOLINES AND DERIVATIVES THEREOF, COMPOSITIONS AND METHODS

(75) Inventor: Owen Brendan Wallace, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/475,593

(22) PCT Filed: May 9, 2002

(86) PCT No.: PCT/US02/11878

§ 371 (c)(1),
(2), (4) Date: Oct. 22, 2003

(87) PCT Pub. No.: WO02/094788

PCT Pub. Date: Nov. 28, 2002

(65) Prior Publication Data

US 2004/0215018 A1 Oct. 28, 2004

Related U.S. Application Data

(60) Provisional application No. 60/292,704, filed on May 22, 2001.

(51) Int. Cl.
C07D 215/06 (2006.01)
C07D 215/08 (2006.01)
A61K 31/47 (2006.01)
A61K 31/4709 (2006.01)

(52) U.S. Cl. ...................... 514/314; 546/168
(58) Field of Classification Search ............... 546/152, 546/153, 156; 514/311, 312, 315, 235.2; 544/128
See application file for complete search history.

(56) References Cited

U.S. PATENT DOCUMENTS

| | | | |
|---|---|---|---|
| 3,819,637 A * | 6/1974 | Bell | 546/165 |
| 3,994,902 A * | 11/1976 | Bell | 546/156 |
| 4,075,227 A | 2/1978 | Jones et al. | |
| 4,133,814 A | 1/1979 | Jones et al. | |
| 4,230,862 A | 10/1980 | Suarez et al. | |
| 4,418,068 A | 11/1983 | Jones | |
| 5,393,763 A | 2/1995 | Black et al. | |
| 5,403,847 A | 4/1995 | Gluchowski et al. | |
| 5,446,053 A | 8/1995 | Keohane | |
| 5,457,116 A | 10/1995 | Black et al. | |
| 5,461,065 A | 10/1995 | Black et al. | |
| 5,482,949 A | 1/1996 | Black et al. | |
| 5,508,306 A | 4/1996 | Chiu et al. | |
| 5,510,357 A | 4/1996 | Palkowitz | |
| 5,523,309 A | 6/1996 | Bryant et al. | |
| 5,567,828 A | 10/1996 | Dodge | |
| 5,686,465 A | 11/1997 | Merand et al. | |
| 5,688,796 A | 11/1997 | Cullinan et al. | |
| 5,723,474 A | 3/1998 | Palkowitz | |
| 5,726,168 A | 3/1998 | Cullinan et al. | |
| 5,728,724 A | 3/1998 | Bryant et al. | |
| 5,811,421 A | 9/1998 | Dodge et al. | |
| 5,840,735 A | 11/1998 | Labrie et al. | |
| 5,843,963 A | 12/1998 | Hauser et al. | |
| 5,843,965 A | 12/1998 | Palkowitz | |
| 5,916,916 A | 6/1999 | Hauser et al. | |
| 5,929,090 A | 7/1999 | Hauser et al. | |
| 5,948,795 A | 9/1999 | Berg et al. | |
| 5,948,796 A | 9/1999 | Bryant et al. | |
| 5,958,916 A | 9/1999 | Bryant et al. | |
| 5,958,969 A | 9/1999 | Bryant et al. | |
| 5,962,475 A | 10/1999 | Schmid et al. | |
| 5,981,570 A | 11/1999 | Bryant et al. | |

(Continued)

FOREIGN PATENT DOCUMENTS

EP 113007 A1 * 7/1984

(Continued)

OTHER PUBLICATIONS

XP002170868; "Structure-Activity-Relationship of Antiestrogens. Effect of the Side Chain and Its Position on the Activity of 2,3-Diaryl-2H-1-Benzopyrans"; Sharma, A.P., et al; Journal of Medicinal Chemistry, American Chemical Society, Washington, U.S.; vol. 33; 1990; pp. 3216-3222.

(Continued)

Primary Examiner—Taofiq Solola
Assistant Examiner—Nyeemah Grazier
(74) Attorney, Agent, or Firm—John C. Demeter

(57) ABSTRACT

The current invention provides novel 2-substituted 1,2,3,4-tetrahydroquinolin-6-ols and derivatives thereof of the formula (I) (A); pharmaceutical compositions thereof, optionally in combination with estrogen or progestin; methods for inhibiting a disease associated with estrogen deprivation; and methods for inhibiting a disease associated with an aberrant physiological response to endogenous estrogen.

(A)

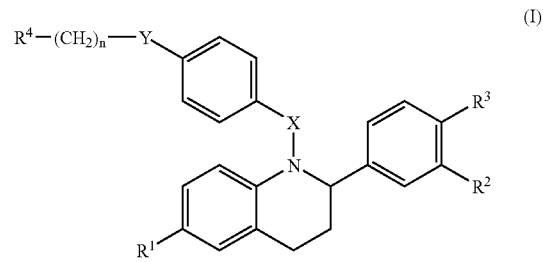

(I)

32 Claims, No Drawings

U.S. PATENT DOCUMENTS

| | | |
|---|---|---|
| 5,985,897 A | 11/1999 | Muehl et al. |
| 5,998,401 A | 12/1999 | Palkowitz |
| 5,998,442 A | 12/1999 | Yong Cho et al. |
| 6,017,914 A | 1/2000 | Bryant et al. |
| 6,025,382 A | 2/2000 | Bastian et al. |
| 6,060,488 A | 5/2000 | Dodge et al. |
| 6,090,843 A | 7/2000 | Bryant et al. |
| 6,303,634 B1 | 10/2001 | Cohen et al. |
| 6,384,053 B1 | 5/2002 | Muehl |
| 6,391,892 B1 | 5/2002 | Bryant et al. |
| 6,395,755 B1 | 5/2002 | Bryant et al. |
| 6,399,634 B1 | 6/2002 | Bryant et al. |
| 6,410,564 B1 | 6/2002 | Bryant et al. |
| 6,417,199 B1 | 7/2002 | Muehl |
| 6,432,982 B1 | 8/2002 | Cullinan et al. |
| 6,432,983 B1 | 8/2002 | Cullinan et al. |
| 6,440,958 B1 | 8/2002 | Jones et al. |
| 6,444,688 B1 | 9/2002 | Dodge et al. |
| 6,479,517 B1 | 11/2002 | Bryant et al. |
| 6,509,356 B1 | 1/2003 | Dodge et al. |
| 6,599,920 B1 | 7/2003 | Bryant et al. |
| 6,608,090 B1 | 8/2003 | Bourgeois et al. |

FOREIGN PATENT DOCUMENTS

| | | |
|---|---|---|
| EP | 0 773 217 A1 | 5/1997 |
| EP | 0 802 183 A1 | 10/1997 |
| EP | 0 802 184 A1 | 10/1997 |
| EP | 0 835 867 A1 | 4/1998 |
| EP | 0 747 380 B1 | 9/1998 |
| EP | 0 729 951 B1 | 6/1999 |
| EP | 1 113 007 | 4/2001 |
| JP | 04 316557 | 11/1992 |
| WO | WO 95/10513 | 4/1995 |
| WO | WO 95/17382 | 6/1995 |
| WO | WO 96/32937 | 10/1996 |
| WO | WO 97/25033 | 7/1997 |
| WO | WO 98 08797 | 3/1998 |
| WO | WO 98/48793 | 11/1998 |
| WO | WO 99/19293 | 4/1999 |
| WO | WO 99/59969 | 11/1999 |

OTHER PUBLICATIONS

XP002211488; *"New 1,2,3,4-tetrahydroquinoline-carboxylic acid Derivatives"*; Derwent Publications, Ltd., London, GB; AN 1992-420416.

* cited by examiner

2-SUBSTITUTED 1,2,3,4-TETRAHYDROQUINOLINES AND DERIVATIVES THEREOF, COMPOSITIONS AND METHODS

This application claims the benefit under 35 U.S.C. §120 of International Application No. PCT/US02/11878 filed May 9, 2002, which claims the benefit under 35 U.S.C. § 119(e) of U.S. Ser. No. 60/292,704, filed May 22, 2001.

BACKGROUND OF THE INVENTION

The present invention relates to 2-substituted 1,2,3,4-tetrahydroquinolines and derivatives thereof, compositions containing those compounds, their use as selective estrogen receptor modulators, and their use in inhibiting bone loss, cardiovascular disease, and breast and uterine carcinoma.

Menopause, the transition in women from the reproductive to the non-reproductive stage of life, is characterized by the cessation of menstruation and occurs at an average age of fifty years. The postmenopausal state is characterized by changes in the levels of circulating sex hormones, the most dramatic of which is the reduction in plasma levels of 17β-estradiol to less than ten percent of premenopausal values. Clinical and epidemiological studies have shown that the postmenopausal state is an important risk factor for a number of chronic disorders, notably osteoporosis and cardiovascular disease. In view of the fact that the current life span of women is about eighty years, women spend approximately one-third of their lives in the postmenopausal state. This means that the potential for chronic effects of the postmenopausal state on women's health is greater today than at the turn of the century when life expectancy was considerably shorter.

Osteoporosis describes a group of diseases which are characterized by the net loss of bone mass per unit volume. The consequence of this loss of bone mass and resulting bone fracture is the failure of the skeleton to provide adequate structural support for the body. The most vulnerable bone tissue to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the biomechanical strength of the overall structure.

Following the cessation of menses, most women lose from about 20% to about 60% of the bone mass in the trabecular compartment of the bone within 3 to 6 years. This rapid loss is generally associated with an increase of bone resorption and formation. However, the resorptive cycle is more dominant and the result is a net loss of bone mass.

In postmenopausal osteoporosis, it is primarily the net resorption and loss of the trabeculae which leads to the failure and fracture of bone. In light of the loss of the trabeculae in postmenopausal women, it is not surprising that the most common fractures are those associated with bones which are highly dependent on trabecular support, for example the vertebrae, the neck, and the weight bearing bones such as the femur and the fore-arm. Indeed, hip fracture, collies fractures, and vertebral crush fractures are hallmarks of postmenopausal osteoporosis.

There are an estimated 25 million women in the United States alone who are afflicted with this disease. The results of osteoporosis are personally harmful and also account for a large economic loss due its chronicity and the need for extensive and long term support (hospitalization and nursing home care). This is especially true in more elderly patients. Additionally, although osteoporosis is not generally thought of as a life threatening condition, a 20% to 30% mortality rate is related with hip fractures in elderly women. A large percentage of this mortality rate can be directly associated with postmenopausal osteoporosis.

Cardiovascular disease is the leading cause of death among women. Compared to men, premenopausal women are relatively protected from cardiovascular disease; however, this protection is gradually lost following menopause. The nature of estrogen's ability to regulate serum lipids is not well understood, but evidence indicates that estrogen can up-regulate the low density lipid (LDL) receptors in the liver which act to remove excess cholesterol. Additionally, estrogen appears to have some effect on the biosynthesis of cholesterol, and other beneficial effects on cardiovascular health.

At the present time, one generally accepted method for treatment of disorders resulting in the postmenopausal state from the decline in estrogen levels is estrogen replacement therapy. The therapy may take the form of administering estrogen alone in so-called unopposed estrogen replacement therapy (ERT) or in the form of coadministering estrogen and progestin in a so-called hormonal replacement therapy (HRT) regimen. There are, however, major liabilities associated with chronic administration of estrogen in postmenopausal women having to do with adverse effects on the breast and uterus. Women on ERT develop endometrial cancer at rates three to six times higher than nonusers after three to six years of use; after ten years of ERT, the risk ratio increases to tenfold.

To combat these deleterious effect of ERT, the coadministration of progestin along with estrogen in a combined hormonal replacement therapy (HRT) is employed, since progestin acts to limit uterine stimulation and thus reduce the risk of uterine cancer.

Because of these known and suspected or feared liabilities of estrogen therapy, prescription of and patient compliance with chronic estrogen replacement therapy has been poor. It has been estimated that, in the United States among postmenopausal women for whom ERT or HRT has been prescribed, fewer than forty percent continue therapy beyond one year.

As a consequence, there is a need for the development of postmenopausal therapy agents which possess the ideal pharmacological profile: for example agents which produce the beneficial effects of estrogen upon skeletal tissue and the cardiovascular system without producing the adverse effects of estrogen upon the breast and the uterus. Agents possessing such an estrogen profile would reverse the effects of estrogen deficiency in certain tissues while at the same time bypassing or failing to act in tissues in which estrogen produces adverse effects. The term selective estrogen receptor modulators or "SERMs" has been applied such compounds which possess this tissue selective profile. SERMs are defined as compounds producing estrogen agonism in one or more desired target tissues such as bone, liver, etc., together with estrogen antagonism and/or minimal (i. e. clinically insignificant) agonism in reproductive tissues such as the breast or uterus.

BRIEF SUMMARY OF THE INVENTION

The present invention provides a compound of the formula

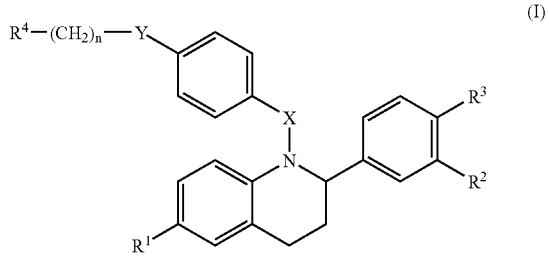

wherein
R$^1$ is —H, —OH, —O(C$_1$–C$_4$ alkyl), —OCOC$_6$H$_5$, —OCO(C$_1$–C$_6$ alkyl), or —OSO$_2$(C$_2$–C$_6$ alkyl);
R$^2$ and R$^3$ are each independently —H, —OH, —O(C$_1$–C$_4$ alkyl), —OCOC$_6$H$_5$, —OCO(C$_1$–C$_6$ alkyl), —OSO$_2$(C$_2$–C$_6$ alkyl) or halo;
R$^4$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;
n is 1, 2 or 3;
X is —C(O)— or —CH$_2$—; and
Y is —O—, —S—, —NH—, —NMe-, or —CH$_2$—;

or an enantiomer or a pharmaceutically acceptable salt thereof.

In a second embodiment, the present invention provides a pharmaceutical composition comprising a therapeutically effective amount of a compound of formula (I), alone or in combination with estrogen or progestin, and a pharmaceutically acceptable carrier.

In a further embodiment, the present invention provides medical methods of employing compounds of the present invention, for alleviating symptoms of estrogen deprivation, including bone loss, for example, osteoporosis; cardiovascular disease, for example hypertension, thrombosis and lowering serum cholesterol.

In an alternative embodiment of the medical method of the present invention, the compounds of the present invention are employed in the treatment of disease conditions associated with an aberrant physiological response to endogenous estrogen including uterine fibroid disease or uterine fibrosis, endometriosis, and estrogen dependent cancers.

DETAILED DESCRIPTION OF THE INVENTION

General terms used in the description of compounds herein described bear their usual meanings. For example, "C$_1$–C$_6$ alkyl" refers to straight or branched aliphatic chains of 1 to 6 carbon atoms including moieties such as methyl, ethyl, propyl, isopropyl, butyl, n-butyl, pentyl, isopentyl, hexyl, isohexyl, and the like. Likewise, "C$_1$–C$_4$ alkyl" refers to straight or branched aliphatic chains of 1 to 4 carbon atoms including moieties such as methyl, ethyl, propyl, isopropyl, butyl, n-butyl, and the like. Similarly, the term "C$_1$–C$_4$ alkoxy" represents a C$_1$–C$_4$ alkyl group attached through an oxygen molecule and include moieties such as, for example, methoxy, ethoxy, n-propoxy, isopropoxy, and the like.

The term "NMe" refers to methylamino.
The term "halo" refers to bromo, chloro, fluoro and iodo.
As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein E$^1$ is the amount of the first enantiomer and E$^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen,"*Stereochemistry of Organic Compounds*", (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The designation "——" refers to a bond that protrudes forward out of the plane of the page.

The designation "······" refers to a bond that protrudes backward out of the plane of the page.

The designation "∼∼∼" refers to a bond wherein the stereochemistry is not defined.

As used herein, the term "estrogen" includes steroidal compounds having estrogenic activity such as, for example, 17β-estradiol, estrone, conjugated estrogen (Premarin®), equine estrogen 17a-ethynyl estradiol, and the like. As used herein, the term "progestin" includes compounds having progestational activity such as, for example, progesterone, norethylnodrel, nongestrel, megestrol acetate, norethindrone, and the like.

Preferred compounds of this invention include compounds of formula I wherein Y is —O—.

Certain $R^3$ and $R^4$ groups also demonstrate preferable characteristics. For example, those compounds of formula I wherein $R^4$ is 1-pyrrolidinyl, 1-hexamethyleneimino, or 1-piperidinyl are preferred. A further preferred subgroup of the preferred 1-pyrrolidinyl, 1-hexamethyleneimino, or 1-piperidinyl compounds include those compounds wherein $R^1$, $R^2$, and $R^3$ are each independently —H, —OH or —OCH$_3$.

Particularly preferred compounds of formula I include those having all of the aforementioned limitations, that is, compounds wherein Y is —O—; $R^1$, $R^2$, and $R^3$ are each independently —H, —OH, or —OCH$_3$, particularly wherein $R^1$ and $R^2$ are —OH and $R^3$ is —H or wherein $R^1$ and $R^3$ are —OH and $R^2$ is —H; and $R^4$ is 1-pyrrolidinyl or 1-piperidinyl.

Although the free-base or acid forms of formula I compounds can be used in the methods of the present invention, it is preferred to prepare and use a pharmaceutically acceptable salt form. Thus, the compounds used in the methods of this invention form pharmaceutically acceptable acid or base addition salts with a wide variety of organic and inorganic acids and bases, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, b-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. Preferred salts are the hydrochloride and oxalate salts.

Typical bases used to form pharmaceutically acceptable addition salts would be inorganic bases, such as, sodium hydroxide, potassium hydroxide, alkali carbonates or bicarbonates, calcium carbonate, magnesium carbonate, and the like. Additionally, organic bases may be utilized to form addition salts, e.g., alkyl amines, such as, triethylamine, dimethylamine, i-propylamine, and the like.

The pharmaceutically acceptable acid or base addition salts are typically formed by reacting a compound of formula I with an equimolar or excess amount of acid or base. The reactants are generally combined in a mutual solvent such as diethyl ether or ethyl acetate. The salt normally precipitates out of solution within about one hour to 10 days and can be isolated by filtration or the solvent can be stripped off by conventional means.

Specific examples of compounds contemplated as falling within the scope of the present invention include, but are not limited to the following compounds and their pharmaceutically acceptable salts:

[6-methoxy-2-(4-methoxyphenyl)-3,4-dihydro-2H-quinolin-1-yl]-[4-(2-piperidin-1-yl-ethoxy)phenyl]methanone;

(6-methoxy-2-phenyl-3,4-dihydro-2H-quinolin-1-yl)-[4-2-piperidin-1-yl-ethoxy)phenyl]methanone;

[6-hydroxy-2-(4-hydroxyphenyl)-3,4-dihydro-2H-quinolin-1-yl]-[4-2-piperidin-1-yl-ethoxy)phenyl]methanone;

(6-hydroxy-2-phenyl-3,4-dihydro-2H-quinolin-1-yl)-[4-(2-piperidin-1-yl-ethoxy)phenyl]methanone;

6-methoxy-2-phenyl-1-[4-(2-piperidin-1-yl-ethoxy)benzyl]-1,2,3,4-tetrahydroquinoline;

6-methoxy-2-phenyl-1-[4-(2-piperidin-1-yl-ethoxy)benzyl]-1,2,3,4-tetrahydroquinoline;

2-(4-hydroxyphenyl)-1-[4-(2-piperidin-1-yl-ethoxy)benzyl]-1,2,3,4-tetrahydroquinolin-6-ol;

2-phenyl-1-[4-(2-piperidin-1-yl-ethoxy)benzyl]-1,2,3,4-tetrahydroquinolin-6-ol;

6-methoxy-2-(4-methoxyphenyl)-1-[4-(2-pyrrolidin-1-yl-ethoxy)benzyl]-1,2,3,4-tetrahydroquinoline;

6-methoxy-2-(3-methoxyphenyl)-1-[4-(2-piperidin-1-yl-ethoxy)-benzyl]-1,2,3,4-tetrahydro-quinoline; and 2-(3-hydroxyphenyl)-1-[4-(2-piperidin-1-yl-ethoxy)-benzyl]-1,2,3,4-tetrahydro-quinolin-6-ol; and 2-(4-hydroxyphenyl)-1-[4-(2-piperidin-1-yl-ethoxy)benzyl]-1,2,3,4-tetrahydroquinolin-6-ol.

The compounds of formula (I) can be prepared by utilizing procedures and techniques well known and appreciated by one of ordinary skill in the art. A general synthetic scheme for preparing compounds of formula (1) wherein X is —(O)— and Y is —O— is set forth in Scheme A, wherein all substituents, unless otherwise indicated, are previously defined.

SCHEME A

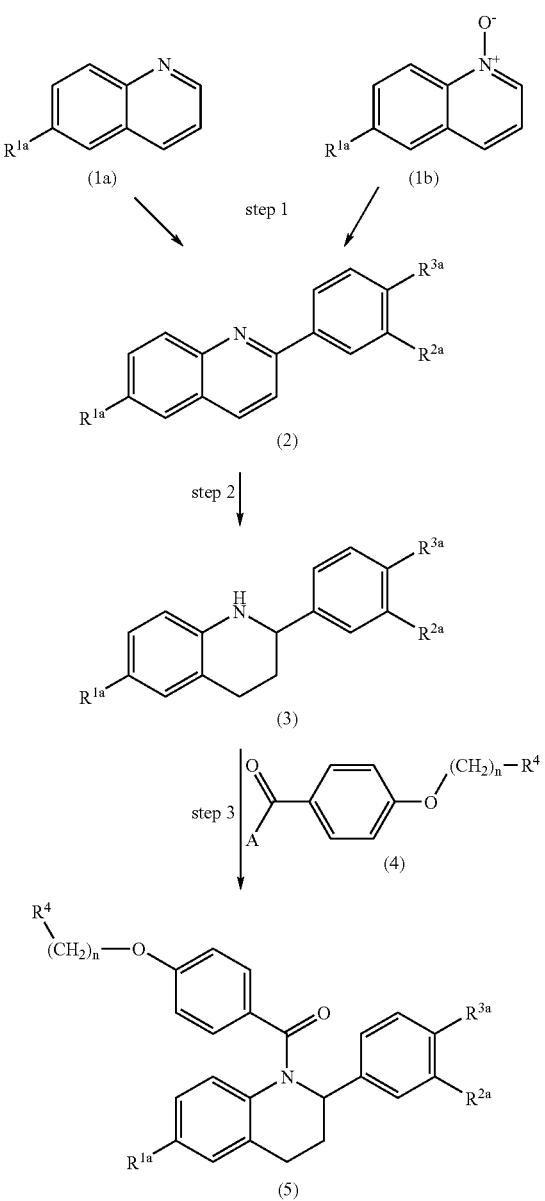

In Scheme A, $R^{1a}$, $R^{2a}$, and $R^{3a}$ are each independently —H, —OH, or —OPg, where Pg is a hydroxy protecting group; and A is a suitable activating group defined more fully below. In compounds of formula (1a), (1b), (2), (3), et seq., the Pg protecting groups $R^{1a}$, $R^{2a}$, and $R^{3a}$ are phenolic protecting groups of the type taught by T. Greene, et al. in Chapter 3 of "Protective Groups in Organic Synthesis," Second Edition, John Wiley & Sons, Inc., New York, 1991, pp.143–170. The preferred protecting groups are alkyl ether groups, with methyl being particularly preferred.

In Scheme A, step 1, the 2-phenylquinoline of formula (2) may be prepared by either reacting $R^{1a}$-substituted quinoline of formula (1a) with a $R^{2a}$, $R^{3a}$-substituted phenyl lithium or $R^{1a}$-substituted quinoline-N-oxide (1b) with a $R^{2a}$, $R^{3a}$-substituted phenyl magnesium halide under Grignard conditions. The Grignard reaction and the reactions using organolithium compounds are of the type taught by Gilman et al., J. Am. Chem. Soc. 68, 2017 (1946); Gilman and Gainer, J. Am. Chem. Soc. 69, 887 (1947); and Comins, D. L., Brown, J. D., Tetrahedron Lett. 27, 4549 (1986).

For example, the $R^{1a}$-substituted quinoline-N-oxide (1b) is reacted with methyl chloroformate at a temperature range of from about −90° C. to about −50° C., more preferably about −78° C. The reaction is typically conducted under anhydrous conditions in a suitable aprotic organic solvent such as anhydrous tetrahydrofuran. The $R^{1a}$-substituted quinoline-N-oxide (1b) and the methyl chloroformate are preferably present in the reaction zone in an approximately equimolar quantity. A slight excess of either reactant is not detrimental to the reaction. The reaction is allowed to proceed for a period of time ranging from about 20 minutes to about 5 hours. A substantially equimolar amount of $R^{2a}$, $R^{3a}$-substituted phenyl magnesium halide is then added. The reaction is then quenched with a proton source such as, for example, sodium bicarbonate or methanol. The solvent is removed and the resulting mixture is extracted, concentrated and purified according to techniques well known in the art.

Appropriate $R^{1a}$-substituted quinolines of formula (1a) and appropriate $R^{1a}$-substituted quinoline-N-oxides (1b) are commercially available or are prepared by techniques and procedures well known in the art.

Further, appropriate $R^{2a}$, $R^{3a}$-substituted phenyl lithiums and $R^{2a}$, $R^{3a}$-substituted phenyl magnesium halides are commercially available or prepared by techniques well known in the art. For example, a solution of the appropriate $R^{2a}$, $R^{3a}$-substituted phenyl is reacted with an organolithium compound such as n-butyllithium or t-butyllithium, more preferably t-butyllithium, for a period of time ranging from about 5 minutes to about 30 minutes and more preferably about 15 minutes; at a temperature range of from about −90° C. to about −50° C., more preferably about −78° C. The organolithium compound will be present in the quantity of from about 1.0 to 1.1 equivalents for every mole of $R^{2a}$, $R^{3a}$-substituted phenyl utilized, and more preferably will be present in an approximately equimolar quantity. The reaction is typically conducted under anhydrous conditions in a suitable aprotic organic solvent such as tetrahydrofuran.

In Scheme A, step 2, the 2-phenyl-1,2,3,4-tetrahydroquinoline of formula (3) is prepared by reducing 2-phenylquinoline of formula (2). For example, 2-phenylquinoline of formula (2) is dissolved in a suitable alcoholic solvent, such as absolute ethanol. Sodium metal is then added and the reaction is allowed to cool to room temperature. The reaction mixture may then be diluted with water and extracted with a suitable organic solvent, such as methylene chloride, ethyl acetate, or chloroform. The combined extracts may then be washed with water and brine, the organic layer is separated and dried and the solvent is evaporated in vacuo to provide the 2-phenyl-1,2,3,4-tetrahydroquinoline of formula (3) which may be used without further purification.

Alternatively, reduction of 2-phenylquinoline of formula (2) may be attained using sodium borohydride in ethanol with nickel chloride catalyst, in a method analogously described by Nose and Kudo, Chem. Pharm. Bull. 36, 1529 (1988).

In Scheme A, step 3, the 1,2-disubstituted-1,2,3,4-tetrahydroquinoline of formula (5) may be prepared by amidating the 2-phenyl-1,2,3,4-tetrahydroquinoline of formula (3) with the substituted benzoyl derivative of compound (4).

For example, 2-phenyl-1,2,3,4-tetrahydroquinoline of formula (3) is reacted with 1 to 1.1 molar equivalents of an appropriate acid derivative of structure (4) as its halide, anhydride, or mixed anhydride. The reaction is carried out in a suitable solvent, such as tetrahydrofuran, dichloromethane, acetone, ethyl acetate, toluene, or diethyl ether. The reaction is carried out in the presence of a base, such as N-methylmorpholine, sodium carbonate, triethylamine, N,N-diisopropylethylamine, potassium carbonate or sodium bicarbonate. The reaction is generally carried out at temperatures of from −78° C. to ambient temperature. Generally, the reactions require 1 to 24 hours. The product (5) can be isolated and purified by techniques well known in the art, such as extraction, evaporation, trituration, chromatography, and recrystallization.

Appropriate compounds of formula (4) can be prepared as described herein from its appropriate benzoic acid derivative as set forth analogously in U.S. Pat. No. 5,962,475, the disclosure of which is hereby incorporated by reference. Appropriate benzoic acid derivatives of compounds of formula (4) are set forth in U.S. Pat. No. 4,418,068, U.S. Pat. No. 5,631,369, and U.S. Pat. No. 5,852,193, the disclosures of which are hereby incorporated by reference.

In compounds of formula (4), the activating group, A, is selected from groups well known in the art to activate acids for the purposes of carrying out amidation reactions and include acid halides such as the fluoride, chloride and bromide; mixed acid anhydrides with $C_1$–$C_6$ alkanoic acids, $C_1$–$C_6$ alkylsulfonic acids, arylsulfonic acids, $C_1$–$C_6$ alkylsulfonic acids, perfluorinated $C_1$–$C_6$ alkanoic acids, $C_1$–$C_6$ alkylcarbonates, arylcarbonates, and the like. The preferred compounds of formula (4) are those in which A is halogen, most preferably chlorine.

A general synthetic scheme for preparing compounds of formula (I) wherein X is —C(O)— and Y is —S—, —$CH_2$—, —NH—, or —NMe- is analogously described in U.S. Pat. No. 5,962,475 and is further set forth in Scheme B, wherein all substituents, unless otherwise indicated, are previously defined.

SCHEME B

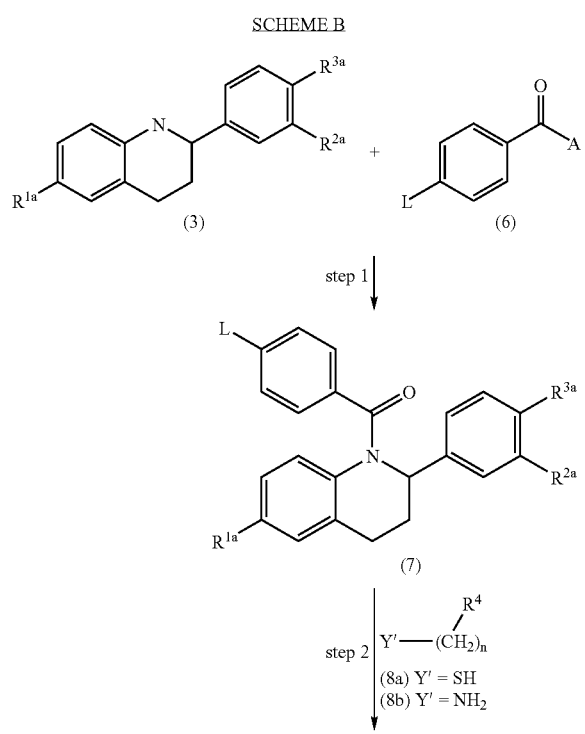

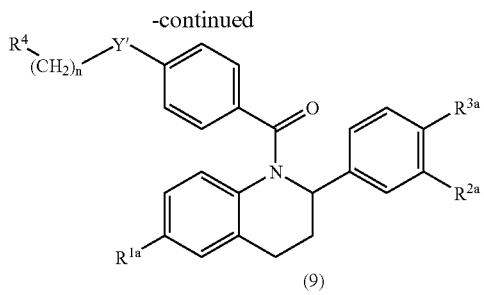

The leaving group, L, in compounds of formula (6) is selected from those groups known in the art to participate in nucleophilic aromatic substitution reactions (see J. March, "Advanced Organic Chemistry," 3rd Edition, John Wiley & Sons, New York, 1985, p. 587. Suitable leaving groups include fluoro, chloro, bromo, nitro, (lower alkyl)phenylsulfonyl, (lower alkyl)sulfonyl, phenylsulfonyl, azido, trialkylammonium, phenoxy, alkoxy, thioalkoxy, and amino.

For purposes of the present invention, the preferred leaving groups include fluoro, chloro, bromo, nitro, (lower alkyl)phenylsulfonyl, and lower alkylsulfonyl, with fluoro, bromo, and nitro being most preferred.

In compounds of formula (6), the activating group, A, is as defined above for the compounds of formula (4) in Scheme A.

In Scheme B, step 1,2-(L-substituted phenyl)-1,2,3,4-tetrahydrofuran (7) may be prepared by amidating the 2-phenyl-1,2,3,4-tetrahydroquinoline of formula (3) with the activated benzoyl derivative of formula (6) according to the procedure set forth in Scheme A, step 3.

In Scheme B, step 2, the product resulting from the amidation reaction, (7), is reacted next with a compound of formula (8) in which $R^4$ and n have the meanings ascribed to them above. In the case where Y' is —SH in compounds of formula (8a), the reaction between (7) and (8a) is carried out by mixing the two reagents in the presence of a strong base in a polar aprotic solvent. Suitable strong bases include alkyllithiums, alkali metal amides, or metal hydrodies such as lithium, potassium or sodium hydride, or lithium aluminum hydride or sodium aluminum hydride.

Suitable polar aprotic solvents include N,N-dimethylformamide, N-methyl pyrrolidinone, N,N'-dimethylpropylurea, dimethylsulfoxide, tetrahydrofuran, and the like.

Alternatively, the sulfhydryl compound, (8a), can be separately converted to the corresponding anion by reaction with a strong base in a polar aprotic solvent, and the resulting anion subsequently reacted with compound (7).

In the case where Y' is —$NH_2$, as in compound (8b), the preferred reaction conditions involve reaction of (7) with (8b) in dimethylsulfoxide in the presence of the phase transfer reagent 18-crown-6 and 37% potassium fluoride adsorbed on alumina at a temperature of about 120° C.

Following the acylation reaction between compounds (3) and (4) in Scheme A, step 3 or between compounds (7) and (8) of Scheme B, step 2, the protecting groups of the resulting products, (5) or (9), may be removed by methods taught in the art to produce the deprotected analogs thereof (for deprotection reagents and reaction conditions, see T. Greene, et al. cited above and the references cited therein). In the case where $R^{1a}$, $R^{2a}$ and/or $R^{3a}$ are the preferred protecting group, methyl, the deprotective removal of the methyl groups can be carried out either by the use of an alkali metal ethanethiolate (see G. I. Fetruell, et al., *Tetra-* hedron Letters, 1327 (1970); idem. Aust. J. Chem., 25: 1719 (1972) and A. S. Kende, et al., Tetrahedron Letters, 22: 1779 (1981) or by the use of either boron tribromide in methylene chloride at a temperature of between about −80° C. to 20° C. for a period of 6–12 hours (J. F. W. McOmie, et al., Org. Syn. Coll. Volume V, 412 (1973)) or BBr$_3$.S(CH$_3$)$_2$ in ethylene chloride at a temperature of about 80° C. to 85° C. (P. G. Williard, et al., Tetrahedron Letters, 21: 3731 (1981)).

Compounds of the present invention wherein X is —CH$_2$— are prepared according to the procedure set forth in Scheme C. In Scheme C, all substituents, unless otherwise indicated, are previously defined.

The acylation reactions which provide the aforementioned R$^1$, R$^2$, and/or R$^3$ groups are carried out at moderate temperatures in the range from about −25° C. to about 100° C., frequently under an inert atmosphere such as nitrogen gas. However, ambient temperature is usually adequate for the reaction.

Such acylations of the hydroxy group also may be performed by acid-catalyzed reactions of the appropriate carboxylic acids in inert organic solvents or neat. Acid catalysts such as sulfuric acid, polyphosphoric acid, methanesulfonic acid, and the like are used.

SCHEME C

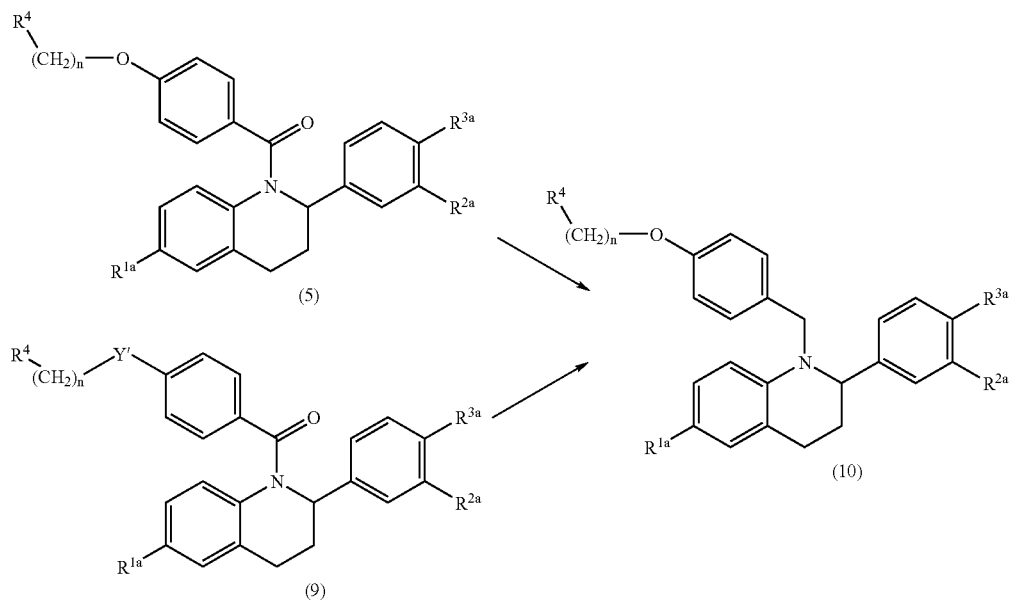

Compounds of the present invention in which X is —CH$_2$— are prepared by dissolution of compounds of formulae (5) or (9) in an appropriate solvent, preferably anhydrous tetrahydrofuran, and reaction with a reducing agent, such as, for example, lithium aluminum hydride, under an inert gas such as nitrogen. The reduced product (10) can be isolated and purified by techniques well known in the art, such as extraction, evaporation, trituration, chromatography, and recrystallization.

When a —OC(O)(C$_1$–C$_6$ alkyl) or —OC(O)C$_6$H$_5$ group is desired at R$^1$, R$^2$, and/or R$^3$ a mono-, di-, or trihydroxy compound of formula I, is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger, such as a tertiary amine, has been added. If desired, acylation catalysts such as 4-dimethylaminopyridine or 4-pyrrolidinopyridine may be used. See, e.g., Haslam, et al., Tetrahedron, 36:2409–2433 (1980).

The aforementioned R$^1$, R$^2$, and/or R$^3$ groups also may be provided by forming an active ester of the appropriate acid, such as the esters formed by such known reagents as dicyclohexylcarbodiimide, acylimidazoles, nitrophenols, pentachlorophenol, N-hydroxysuccinimide, and 1-hydroxybenzotriazole. See, e.g., Bull. Chem. Soc. Japan, 38:1979 (1965), and Chem. Ber., 788 and 2024 (1970).

When a compound is desired in which R$^1$, R$^2$, and/or R$^3$ are —OSO$_2$(C$_4$–C$_6$ alkyl), the suitable starting mono-, di- or trihydroxy compound is reacted with, for example, a derivative of the appropriate sulfonic acid such as a sulfonyl chloride, bromide, or sulfonyl ammonium salt, as taught by King and Monoir, J. Am. Chem. Soc. 97:2566–2567 (1975). The mono-, di- or trihydroxy compound also can be reacted with the appropriate sulfonic anhydride. Such reactions are carried out under conditions such as were explained above in the discussion of reaction with acid halides and the like.

Compounds of formula I can be prepared so that R$^1$, R$^2$, and/or R$^3$ are different biological protecting groups or, preferably, the same biological protecting group. Preferred protecting groups include —CH$_3$, —C(O)C(CH$_3$)$_3$, —C(O)C$_6$H$_5$, and —SO$_2$(CH$_2$)$_3$CH$_3$.

Examples. All reactions are carried out under a nitrogen atmosphere. All solvents are ACS grade and are used as supplied. All reagents are commercially available and used without further purification unless otherwise noted. LCMS data is recorded on a Hewlett Packard 1100 series at 35° C. The method used is 5% acetonitrile-95% water (0.05% TFA) to 95% acetonitrile-5% water (0.05% TFA) over two minutes and hold for three minutes on a Waters Symmetry C18 2.1×50 mm column. ¹H NMR spectra are recorded at 400 MHz on a Varian 400 spectrometer in CDCl₃ (∂7.26) unless otherwise noted.

Preparation 1

6-Methoxy-2-(4-methoxy-phenyl)-quinoline

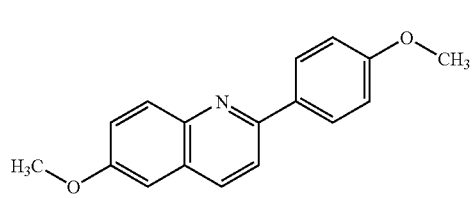

A 500 mL round-bottom flask is charged with 6-methoxy quinoline-N-oxide (8 g, 0.04566 mol.) and placed under nitrogen. The solid is then dissolved in anhydrous THF (100 mL) and cooled to −78° C. with a dry ice/acetone bath, whereupon some of the dissolved solid begins to precipitate. From an addition funnel, methylchloroformate (4.4 ml, 0.05694 mol.) is added dropwise. The bath is removed 10 minutes after the addition, and replaced after 20 minutes. A dropwise addition of 0.5 M anisylmagnesium bromide (112 mL, 0.0560 mol.) is then made. The bath is removed after the addition and the reaction is allowed to warm to room temperature. The reaction is quenched with 5% sodium bicarbonate solution. The THF is removed in vacuo and the resulting mixture is diluted with water and extracted with methylene chloride. The extracts are collected and dried with anhydrous sodium sulfate and concentrated. The crude product is purified by flash chromatography (2–5% EtOAc/dichloromethane) to yield 6.30 g (52%) of the desired product. ¹H NMR: ∂ 8.03–8.11 (m, 4H), 7.78 (d, J=8.8 Hz, 1H), 7.37 (dd, J=9 Hz, 3 Hz, 1H), 7.03–7.07 (m, 3H), 3.94 (s, 1H), 3.88 (s, 1H). LCMS: 2.188 min, 266 (M+).

Preparation 2

6-Methoxy-2-pheyl-quinoline

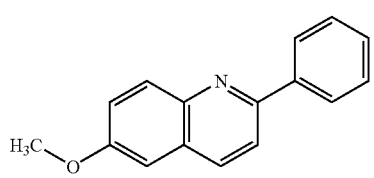

6-Methoxy-2-phenyl quinoline is prepared in a manner analogous to that of Preparation 1 using phenyl magnesium bromide. ¹H NMR: ∂ 8.07–8.15 (m, 4H), 7.84 (d, J=8.8 Hz, 1H), 7.50–7.54 (m, 2H), 7.42–7.46 (m, 1H), 7.39 (dd, J=9 Hz, 3 Hz, 1H), 7.10 (d, J=2.4 Hz, 1H), 3.95 (s, 3H).

Preparation 3

6-Methoxy-2-(4-methoxyphenyl)-1,2,3,4-tetrahydro-quinoline

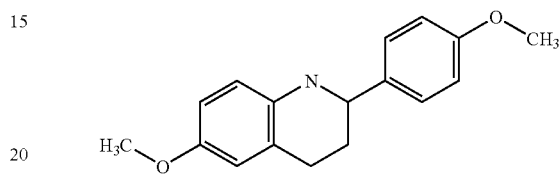

A 500 mL round-bottom flask is charged with the compound of Preparation 1 (3 g, 0.01131 mol) and absolute ethanol (150 mL). The mixture is placed under nitrogen and brought to reflux. Sodium metal pellets are added periodically until no starting material remains by TLC (30% EtOAc/hexanes). The reaction is cooled to room temperature, diluted with water, and extracted with methylene chloride. The combined extracts are then washed with water and brine. The organic is separated and dried with anhydrous sodium sulfate. The solvent is removed in vacuo to yield 3.05 g (100%) of a gold oil. No purification is necessary. ¹H NMR: ∂ 7.32 (app. d, J=8.4 Hz, 2H), 6.89 (app. d, J =8.8 Hz, 2H), 6.61–6.65 (m, 2H), 6.49 (d, J=8.4 Hz, 1H), 4.31 (dd, J=10 Hz, 2.8 Hz, 1H), 3.81 (s, 3H), 3.75 (s, 3H), 2.90–2.99 (m, 1H), 2.73 (dt, J=16.4 Hz, 4.6 Hz, 1H), 2.04–2.10 (m, 1H), 1.91–2.01 (m, 1H).

Preparation 4

6-Methoxy-2-phenyl-1,2,3,4-tetrahydroquinoline

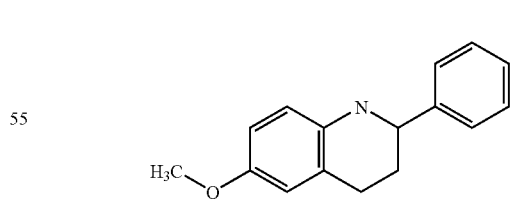

6-Methoxy-2-phenyl-1,2,3,4-tetrahydro-quinoline is prepared in a manner analogous to that of Preparation 3 using 6-Methoxy-2-phenyl quinoline. ¹H NMR: ∂ 7.28–7.43 (m, 5H), 6.63–6.67(m, 2H), 6.52 (d, J=8.8 Hz, 1H), 4.38 (dd, J=9.0 Hz, 3.0 Hz, 1H), 3.76 (s, 3H), 2.91–3.00 (m, 1H), 2.74 (dt, J=16.8 Hz, 4.6 Hz, 1H), 2.09–2.15 (m, 1H), 1.95–2.05 (m, 1H).

Preparation 5

4-(2-piperidin-1-yl-ethoxy)-benzoyl chloride hydrochloride

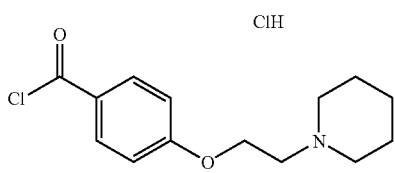

A 500 mL round-bottom flask is charged with 4-(2-piperidin-1-yl-ethoxy)-benzoic acid hydrochloride, (25 g, 0.08748 mol) and thionyl chloride (150 mL, 2.0564 mol). The mixture is brought to reflux for 15 minutes whereupon it becomes a clear solution. The reaction is cooled to room temperature and the excess thionyl chloride is removed to give a quantitative yield of the desired product. $^1$H NMR: $\partial$ 8.08 (app. d, J=8.8 Hz, 2H), 6.99 (app. d, J=9.2 Hz, 2H), 4.71 (t, J=4.6 Hz, 2H), 3.65 (d, J=12 Hz, 2H), 3.43 (quart., J=4.6 Hz, 2H), 2.76–2.85 (m, 2H), 2.22–2.32 (m, 2H), 1.87–1.94 (m, 3H), 1.37–1.49 (m, 1H).

EXAMPLE 1

[6-Methoxy-2-(4-methoxyphenyl)-3,4-dihydro-2H-quinolin-1-yl]-[4-4-(2-piperidin-1-yl-ethoxy)phenyl]methanone

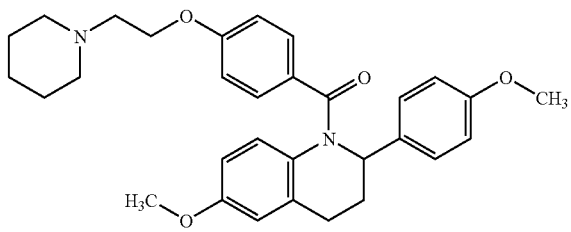

A 250 mL round-bottom flask is charged with the compound of Preparation 3 (3.05 g, 0.01132 mol), 4-(2-piperidin-1-yl-ethoxy)-benzoyl chloride hydrochloride (4.5 g, 0.01479 mol), dichloromethane (125 mL), and triethylamine (10 mL, 0.07175). The stirred solution is placed under nitrogen and followed by LC/MS until no starting material remained. The reaction is washed with saturated sodium carbonate solution, water, and brine. The organic is separated and dried with anhydrous sodium sulfate and concentrated. The crude product is purified by flash chromatography (0–5% MeOH/dichloromethane) to yield 5.33 g (92%) of the desired product. $^1$H NMR: $\partial$ 7.21 (d, J=8.8 Hz, 2H), 7.14 (app. d, J=8.4 Hz, 2H), 6.79 (app. d, J=8.8 Hz, 2H), 6.70 (app. d, J=8.8 Hz, 4H), 6.50 (dd, J=8.4 Hz, 2.4 Hz, 1H), 5.62 (app. t, J=7.6 Hz, 1H), 4.06 (t, J=6 Hz, 2H), 3.75 (s, 3H), 2.74 (t, J=6 Hz, 2H), 2.57–2.80 (m, 3H), 2.49 (m, 4H), 1.92–2.02 (m, 1H), 1.59 (quint. J=5.6 Hz, 4H), 1.40–1.46 (m, 2H). LCMS: 2.247 min, 501 (M+).

EXAMPLE 2

(6-Methoxy-2-phenyl-3,4-dihydro-2H-quinolin-1-yl)-[4-2-piperidin-1-yl-ethoxy)phenyl]methanone

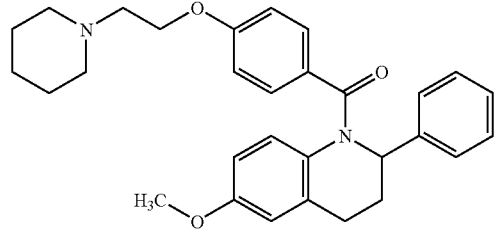

A 250 mL round-bottom flask is charged with the compound of Preparation 4 (3.05 g, 0.01274 mol), 4-(2-piperidin-1-yl-ethoxy)-benzoyl chloride hydrochloride (4.65 g, 0.01529 mol), dichloromethane (100 mL), and triethylamine (10 mL, 0.07175 mol). The reaction is stirred overnight under nitrogen. The reaction is incomplete. 4-(2-piperidin-1-yl-ethoxy)-benzoyl chloride hydrochloride (3 g, 0.009861 mol) and triethylamine (10 mL, 0.07175 mol) are added and the reaction is refluxed. The reaction is washed with sat. sodium bicarbonate solution, water, and brine. The organic is separated and dried with sodium sulfate. The solution is concentrated and the crude product isolated by flash chromatography on silica (0–5% methanol/dichloromethane). The product contains ~33% of 4-(2-piperidin-1-yl-ethoxy)-benzoic acid methyl ester as an inseparable impurity [LC/MS: 1.815 min., 264 (M+)]. The product is carried on without any further purification. $^1$H NMR: $\partial$ 7.16–7.27 (m, 7H), 6.70 (app. d, J=8.4 Hz, 4H), 6.51 (dd, J=8.6 Hz, 2.6 Hz, 1H), 5.66 (t, J=7 Hz, 1H), 4.07 (t, J=5.8 Hz, 2H), 3.75 (s, 3H), 2.61–2.81 (m, 5H), 2.50 (s, 4H), 1.94–2.03 (m, 1H), 1.57–1.64 (m, 4H), 1.40–1.49 (m, 2H), LCMS: 2.253 min, 471 (M+).

EXAMPLE 3

[6-Hydroxy-2-(4-hydroxyphenyl)-3,4-dihydro-2H-quinolin-1-yl]-[4-2-piperidin-1-yl-ethoxy)phenyl]methanone

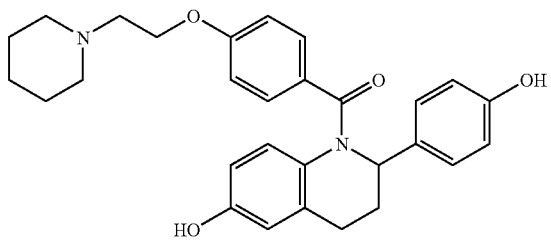

A 25 ml round-bottom flask is charged with the compound of Example 1 (41.3 mg, 0.0824 mmol) and dichloromethane (10 mL). The solution is cooled to 0° C. and 1.0M boron tribromide (0.50 mL, 0.50 mmol) is added. The reaction is allowed to warm to room temperature. The reaction is followed by LCMS. An equal amount of boron tribromide is again added after cooling the reaction to 0° C. This is done three more times over the course of several hours until the reaction appeared complete by LCMS. The reaction is neutralized with methanol and the solvent removed. The residue is taken up in ethyl acetate and washed with water. The water is extracted several times with ethyl acetate. The solvent is concentrated and the material is purified by reverse phase HPLC. An amount of 10.6 mg is obtained as the TFA salt. $^1$H NMR [CD$_3$OD ($\partial$ 3.30)]: $\partial$ 7.22 (d, J=8.4 Hz, 2H), 7.02 (d, J=8.8 Hz, 2H), 6.88 (d, J=8.4 Hz, 2H), 6.65–6.78 (m, 4H), 6.30–6.36 (m, 1H), 5.45–5.49 (broad s, 1H), 4.33 (t, J=4.6 Hz, 2H), 3.60 (d, J=12.4 Hz, 2H), 3.53 (t, J=4.6 Hz, 2H), 3.00–3.10 (m, 2H), 2.60–2.80 (m, 4H), 1.70–2.00 (m, 5H), 1.45–1.60 (m, 1H). LCMS: 2.131 min., 473 (M+).

EXAMPLE 4

(6-Hydroxy-2-phenyl-3,4-dihydro-2H-quinolin-1-yl)-[4-2-piperidin-1-yl-ethoxy)phenyl]methanone

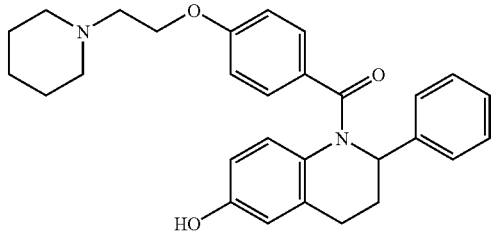

To a solution of the compound of Example 2 (10 mg, 0.02125 mmol) in dichloromethane (1 ml) at room temperature is added boron tribromide (0.20 ml, 0.20 mmol) dropwise. The reaction is stirred for 30 minutes after which time TLC shows no starting material remained. The mixture is diluted with dichloromethane and washed with sat. sodium bicarbonate solution, water, and brine. The organic phase is then dried over sodium sulfate, filtered and concentrated. The crude product is purified by flash chromatography (100% ethyl acetate) to yield 7.9 mg (81%) of product. $^1$H NMR $\partial$ 7.13–7.27 (m, 7H), 6.52–6.60 (m, 4H), 6.24 (dd, J=10 Hz, 2 Hz, 1H), 5.61 (t, J=9 Hz, 1H) 4.00–4.10 (m, 2H), 2.76–2.83 (m, 1H), 2.43–2.74 (m, 8H), 1.82–1.93 (broad m, 1H), 1.58–1.67 (broad m, 4H), 1.39–1.49 (broad m, 2H). LCMS: 2.321 min., 457 (M+).

EXAMPLE 5

6-Methoxy-2-phenyl-1-[4-(2-piperidin-1-yl-ethoxy)-benzyl]-1,2,3,4-tetrahydroquinoline hydrochloride

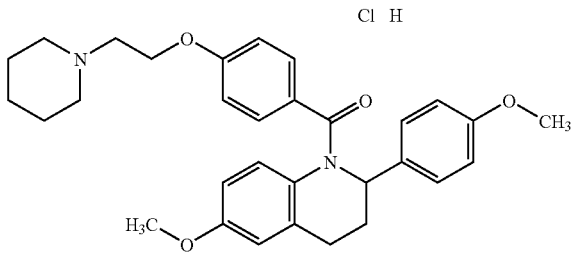

A 250 ml round-bottom flask is charged with the compound of Example 1 (5.22 g, 0.01043 mol) in 75 mL of anhydrous THF followed by the addition of LiAlH$_4$ (0.80 g, 0.02108). The reaction mixture is then brought to reflux for 15 minutes. LC/MS confirms the consumption of the starting material. The reaction is cooled and quenched with ice. The solids are removed by filtration and the filtrate is concentrated. The crude product is purified by flash chromatography (0–5% MeOH/dichloromethane). The product elutions are collected and the solvent removed in vacuo to yield an oil. The oil is taken up in ether and an excess of 1.0 M HCl in ether is added. The hydrochloride salt of the product precipitates and is collected by filtration. The solid is washed with ether and hexanes. An amount of 1.5571 g (30.7%) is obtained. $^1$H NMR [CD$_3$OD ($\partial$ 3.30)]: $\partial$ 6.60–7.53 (broad m, 11H), 4.60–4.23 (m, 2H), 4.40 (s, 2H), 3.84 (s, 6H), 3.58–3.64 (m, 6H), 3.09 (t, J=12 Hz, 4H), 2.40–2.61 (broad s, 1H), 1.80–2.01 (m, 5H), 1.50–1.60 (m, 1H). LCMS: 2.421 min., 487 (M+).

EXAMPLE 6

6-Methoxy-2-phenyl-1-[4-(2-piperidin-1-yl-ethoxy)-benzyl]-1,2,3,4-tetrahydroquinoline hydrochloride

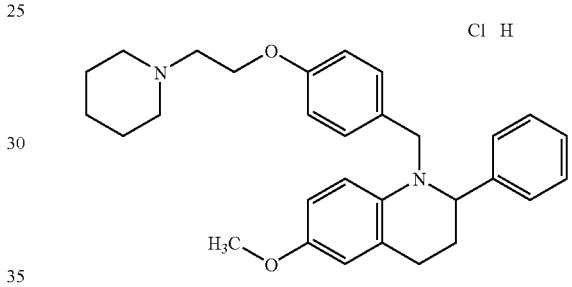

6-Methoxy-2-phenyl-1-[4-(2-piperidin-1-yl-ethoxy)-benzyl]-1,2,3,4-tetrahydroquinoline hydrochloride is prepared in a manner analogous to that of Example 5 using the compound of Example 2. $^1$H NMR [CD$_3$OD ($\partial$ 3.30)]: $\partial$ 6.50–7.90 (broad m, 12H), 4.40 (t, J=4.8 Hz, 2H), 3.68–4.00 (broad s, 2H), 3.56–3.64 (m, 6H), 3.30 (s, 3H), 3.08 (t, J=11 Hz, 4H), 2.35–2.74 (broad s, 1H), 1.80–1.98 (m, 5H), 1.30–1.60 (m, 1H), LCMS: 2.446 min, 457 (M+).

EXAMPLE 7

2-(4-Hydroxy-phenyl)-1-[4-(2-piperidin-1-yl-ethoxy)-benzyl)-1,2,3,4-tetrahydroquinolin-6-ol

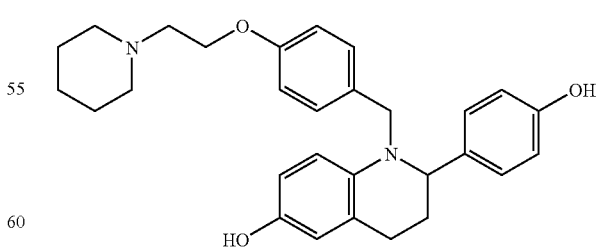

A 100 round-bottom flask is charged with the compound of Example 5 (1.5571 g, 0.003200 mol) and 30 ml of dichloromethane. The solution is placed under nitrogen and cooled to 0° C. before adding boron tribromide (1.5 ml, 0.01587 mol). The reaction is followed by LC/MS until complete. The reaction is quenched with methanol and saturated sodium bicarbonate solution and extracted with 1% methanol in dichloromethane. The extracts are dried with anhydrous sodium sulfate and preadsorbed onto silica gel. The material is then purified by flash chromatography (0–5% methanol/dichloromethane). The solid is removed to give a red/orange solid. The solid is washed with acetonitrile which removed much of the red color. An amount of 704.2 mg (50%) is obtained. $^1$H NMR [CD$_3$OD ($\partial$ 3.30)]: $\partial$ 7.09 (d, J=8.8 Hz, 2H), 6.98 (d, J=8.8, 2H), 6.82 (d, J=8.4 Hz, 2H), 6.69 (d, J=8.8 Hz, 2H), 6.38–6.45 (m, 3H), 4.45–4.50 (m, 2H), 4.02–4.10 (m, 3H), 2.76 (t, J=5.6 Hz, 2H), 2.52–2.55 (m, 6H), 2.11–2.19 (m, 1H), 1.95–2.01 (m, 1H), 1.63 (quint., J=5.6 Hz, 4H), 1.48 (app. d, J=4.8 Hz, 2H). LCMS: 2.032 min, 459 (M+).

EXAMPLE 8

2-Phenyl-1-[4-(2-piperidin-1-yl-ethoxy)-benzyl]-1,2,3,4-tetrahydroquinolin-6-ol

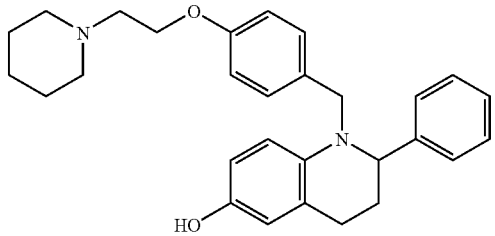

2-Phenyl-1-[4-(2-piperidin-1-yl-ethoxy)-benzyl]-1,2,3,4-tetrahydroquinolin-6-ol is prepared in a manner analogous to that of Example 7 using the compound of Example 6.

$^1$H NMR [CD$_3$OD ($\partial$ 3.30)]: $\partial$ 7.25–7.28 (m, 2H), 7.16–7.21 (m, 3H), 7.10 (d, J=8.4 Hz, 2H), 6.83 (d, J=8.4 Hz, 2H), 6.41–6.46 (m, 3H), 4.50–4.56 (m, 2H), 4.03–4.10 (m, 3H), 3.28–3.31 (m, 1H), 2.45–2.55 (m, 6H), 2.17–2.25 (m, 1H), 2.01–2.06 (m, 1H), 2.76 (t, J=5.6 Hz, 2H), 1.63 (quint., J=5.7 Hz, 4H), 1.48 (app. d, J=4.8 Hz, 2H). LCMS: 2.287 min, 443 (M+).

Preparation 6

1-(4-Benzyloxy-benzyl)-6-methoxy-2-(4-methoxyphenyl)-1,2,3,4-tetrahydroquinoline

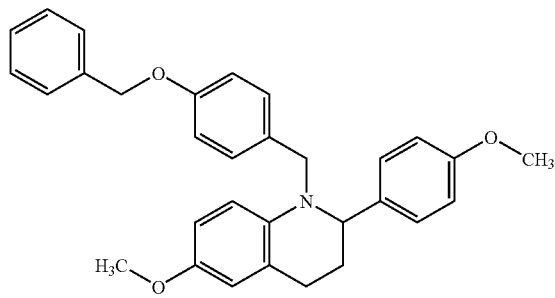

A 50 mL round-bottom flask is charged with the compound of Preparation 3 (165.0 mg, 0.6126 mmol), 4-benzyloxybenzyl chloride (299.0 mg, 1.285 mmol), and anhydrous THF (15 mL) and placed under nitrogen. To this solution, 1.0 M Phosphazine-P$_4$ t-butyl base (0.55 ml of 1M/hexanes, 0.55 mmol) is added. The reaction is checked by TLC (dichloromethane) after two hours. No starting material is present. The reaction is preadsorbed onto silica and the product isolated by flash chromatography (50–75% dichloromethane/hexanes) to yield 287.3 mg (>100%) of product with some minor impurities. $^1$H NMR: $\partial$ 7.36–7.44 (m, 5H), 7.12 (app. t, J=8.8 Hz, 4H), 6.90 (app. d, J= 8.4 Hz, 2H), 6.83 (app. d, J=8.4 Hz, 2H), 6.61–6.40 (m, 2H), 6.49 (d, J=9.6 Hz, 1H), 5.03 (s, 2H), 4.54–4.58 (m, 2H), 4.14 (d, 16.8 Hz, 1H), 3.79 (s, 3H), 3.73 (s, 3H), 2.60–2.64 (m, 2H), 2.19–2.27 (m, 1H), 2.01–2.06 (m, 1H). LCMS: 3.406 min., 466 (M+).

Preparation 7

4-[6-Methoxy-2-(4-methoxyphenyl)-3,4-dihydro-2H-quinolin-1-yl-methyl]phenol

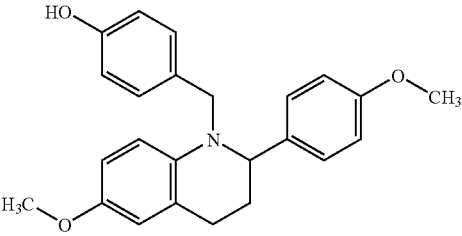

A 25 ml round-bottom flask is charged with the compound of Preparation 6 (287.3 mg, 0.6125 mmol) in ethyl acetate (10 ml), and 10% Pd/C (86 mg, 0.0808 mmol) is added. The mixture is sparged with nitrogen for 10 minutes. The mixture is then periodically sparged with hydrogen gas and kept under constant pressure with a hydrogen filled balloon. The reaction is followed for 3 hours by LCMS. The reaction is then filtered through Celite. The solvent is removed from the filtrate to leave 57.1 mg (24.8%) of the crude desired product as an oil. The product is carried on without purification. $^1$H NMR: $\partial$ 7.08 (t, J=9 Hz, 4H), 6.83 (d, J=8.4 Hz, 2H), 6.75 (d, J=8.4 Hz, 2H), 6.65 (s, 2H), 6.40–6.60 (m, 1H), 4.72 (s, 1H), 4.42–4.68 (m, 2H), 3.79 (s, 3H), 3.60–3.80 (broad m, 3H), 2.60–2.65 (m, 2H), 2.20–2.30 (m, 1H), 2.00–2.05 (m, 1H). LCMS: 2.888 min., 376 (M+).

EXAMPLE 9

6-Methoxy-2-(4-methoxyphenyl)-1-[4-(2-pyrrolidin-1-yl-ethoxy)-benzyl]-1,2,3,4-tetrahydroquinoline

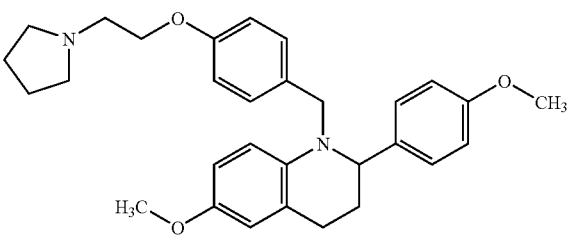

A 50 mL round-bottom flask is charged with the compound of Preparation 7 (57.1 mg, 0.1521 mmol), 1-(2- chloroethyl)-pyrrolidine hydrochloride (85.2 mg, 0.5009 mmol), anhydrous tetrahydrofuran (20 mL), and 1.0M Phosphazine-$P_4$ t-butyl base. The reaction mixture is placed under nitrogen and heated to reflux for 4 hours. The reaction is then allowed to stir at room temperature overnight (14 hours). The reaction is heated to reflux for another two hours. The reaction mixture is preadsorbed onto silica and the product separated by flash chromatography (5–10% dichloromethane/hexanes) to leave an oil contaminated with some unknown impurity. The material is carried on without further purification. Partial $^1$H NMR: ∂ 7.07–7.10 (m, 4H), 6.81–6.84 (m, 4H), 6.61–6.62 (m, 2H), 6.45–6.48 (m, 1H), 3.78 (s, 3H), 3.72 (3H). LCMS: 2.462 min., 2.462 min., 473 (M+).

EXAMPLE 10

2-(4-Hydroxyphenyl)-1-[4-(2-piperidin-1-yl-ethoxy)-benzyl]-1,2,3,4-tetrahydroquinolin-6-ol

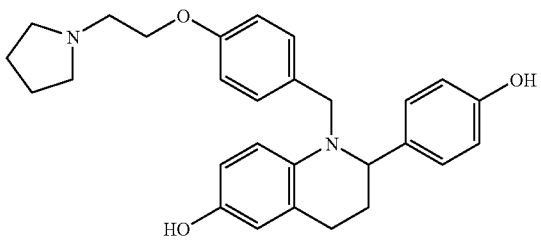

In a 50 mL round-bottom flask, the compound of Example 9 is dissolved in dichloromethane (15 mL) and 1.0M boron tribromide (0.80 mL, 0.80 mmol) is added. After ½ hour, more boron tribromide (0.30 mL, 0.30 mmol) is added. The reaction is followed by LCMS until no starting material is present. The reaction is then quenched with methanol. The mixture is then preadsorbed onto silica gel and separated by flash chromatography (10–20% methanol/dichloromethane) twice. Finally, a third purification is made by flash chromatography (acetone, 20% methanol/dichloromethane). The product is then purified by reverse-phase chromatography to give 16.2 mg as the TFA salt. Partial $^1$H NMR [$CD_3OD$ (∂ 3.30)]: ∂ 7.16 (d, J=8 Hz, 2H), 6.97–7.01 (m, 2H), 6.94 (d, J=8.8 Hz, 2H), 6.70 (d, J=8.8 Hz, 2H), 6.38–6.49 (m, 3), 4.48–4.52 (m, 2H), 4.29 (t, J=4.8 Hz, 2H), 4.02–4.07 (m, 1H), 3.65–3.77 (m, 2H), 3.63 (t, J=4.8 Hz, 2H), 3.15–3.23 (m, 2H), 2.57–2.62 (m, 2H), 2.00–2.10 (m, 3H), 2.10–2.30 (m, 3). LCMS: 2.084 min., 445 (M+).

Preparation 8

6-Methoxy-2-(3-methoxy-phenyl)-quinoline

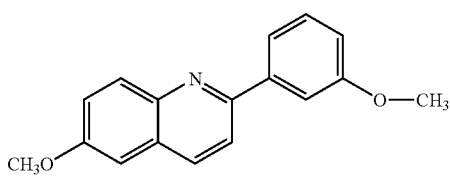

To a solution of 6-methoxyquinoline-N-oxide (175 mg, 1.0 mmol) in THF (3 mL) at room temperature is added methyl chloroformate (77 uL, 1.0 mmol). The mixture is cooled to 0° C. and 3-methoxyphenylmagnesium bromide (2 mL of 1M, 2 mmol) is added dropwise. The mixture is stirred for 16 h while warming to room temperature. The solvent is removed in vacuo and the resulting residue is partitioned between water and $CH_2Cl_2$. The organic phase is washed with water and brine, dried over $MgSO_4$, filtered and concentrated. Flash chromatography (0–20% EtOAc/hexanes) yields 6-methoxy-2-(3-methoxy-phenyl)-quinoline (123 mg, 46% yield).

$^1$H NMR: ∂ 3.90 (s, 3H), 3.92 (s, 3H), 6.97 (app. d, 1H), 7.08 (s, 2H), 7.38 (m, 2H), 7.65 (d, 1H), 7.71 (app. s, 1H), 7.81 (d, 1H), 8.10 (m, 2H).

Preparation 9

6-Methoxy-2-(3-methoxy-phenyl)-1,2,3,4-tetrahydro-quinoline

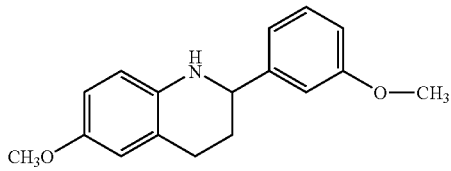

To a stirred solution of 6-methoxy-2-(3-methoxy-phenyl)-quinoline (96 mg, 0.36 mmol) in EtOH (3 mL) at 0° C. is added $NiCl_2·6H_2O$ (86 mg, 0.36 mmol). The reaction mixture is stirred for 30 min before the addition of $NaBH_4$ (55mg, 1.45 mmol). The mixture is stirred for 16 h while warming to room temperature. An additional portion of $NaBH_4$ (50 mg) is then added and stirring is continued for 3 h. The solvent is removed in vacuo and the resulting residue is partitioned between water and $CH_2Cl_2$. The organic phase is washed with water and brine, dried over $MgSO_4$, filtered and concentrated. Flash chromatography (0–50% EtOAc/hexanes) yields 6-methoxy-2-(3-methoxy-phenyl)-1,2,3,4-tetrahydro-quinoline.

$^1$H NMR: ∂ 1.95 (m, 1H), 2.08 (m, 1H), 2.71 (m, 1H), 2.2.90 (m, 2H), 3.7 s (s, 3H), 3.81 (s, 3H), 4.34 (dd, 1H), 6.50 (d, 2H), 6.71 (m, 2H), 6.81 (dd, 1H), 6.95 (m, 2H), 7.25 (m, 1H).

EXAMPLE 11

6-Methoxy-2-(3-methoxy-phenyl)-1-[4-(2-piperidin-1-yl-ethoxy)-benzyl]-1,2,3,4-tetrahydro-quinoline

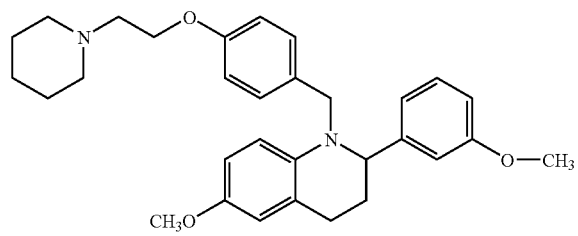

To a solution of 6-methoxy-2-(3-methoxy-phenyl)-1,2,3,4-tetrahydro-quinoline (20 mg, 0.074 mmol) in THF (1.5 mL) at room temperature is added 1-[2-(4-chloromethylphenoxy)-ethyl]-piperidine hydrochloride (PCT Int. Appl. Publ. No. WO 99/19293) (43 mg, 0.149 mmol) followed by phosphazene P1 base (150 mg). The mixture is then heated to 60° C. for 18 h. The crude product is then loaded on a silica gel column and is eluted with 0–100% EtOAc/hexanes to yield 6-methoxy-2-(3-methoxy-phenyl)-1-[4-(2-piperidin-1-yl-ethoxy)-benzyl]-1,2,3,4-tetrahydro-quinoline which is contaminated with an unidentified byproduct.

Partial $^1$HNMR: ∂ 1.44 (br. m), 1.63 (br. m, 4H), 2.51 (br. m), 3.72 (s, 3H), 3.75 (s, 3H), 4.08 (m), 4.58 (m), 6.50 (d), 6.63 (m), 6.73 (s), 6.78 (d), 6.84 (d), 6.88 (d), 7.10 (d), 7.2–7.3 (m).

EXAMPLE 12

2-(3-Hydroxy-phenyl)-1-[4-(2-piperidin-1-yl-ethoxy)-benzyl]-1,2,3,4-tetrahydro-quinolin-6-ol

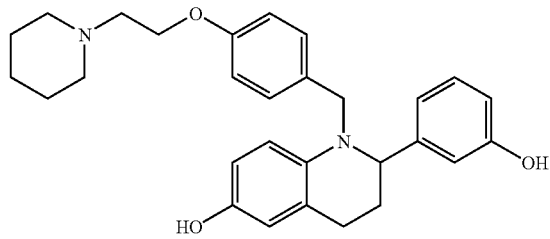

To a solution of 6-methoxy-2-(3-methoxy-phenyl)-1-[4-(2-piperidin-1-yl-ethoxy)-benzyl]-1,2,3,4-tetrahydro-quinoline (18 mg, 0.037 mmol) in $CH_2Cl_2$ at room temperature is added $AlCl_3$ (25 mg) followed by propanethiol (50 uL). The reaction mixture is stirred at room temperature for 3 hours and is then quenched with MeOH. The product is then loaded on a silica gel column and is eluted with 0–30% MeOH/EtOAc to yield 33 mg of product. The product is then further purified by reverse phase prep. HPLC to afford the trifluoracetate salt of 2-(3-hydroxy-phenyl)-1-[4-(2-piperidin-1-yl-ethoxy)-benzyl]-1,2,3,4-tetrahydro-quinolin-6-ol (9.8 mg, 46% yield).

$^1$H NMR ($CD_3OD$): ∂ 1.50 (br. m, 1H), 1.80 (br. m, 3H), 1.92 (br. m, 2H), 2.08 (br. m, 1H), 2.22 (br. m, 1H) 2.58 (br. s, 2H), 3.03 (br. t, 2H), 3.5–3.6 (m, 4H), 4.08 (br. d, 1H), 4.25 (m, 2H), 4.50 (br. m, 2H), 6.40 (s, 2H), 47 (s, 1H), 6.65 (m, 3H), 6.90 (d, 2H), 7.09 (t, 1H), 7.16 (d, 2H). LCMS: 2.17 min, m/z=459 (M+H)$^+$.

Biological Test Procedure General Preparation Procedure

ER Binding Assay

Competition binding assay is run in a buffer containing 50 mM Hepes, pH 7.5, 1.5 mM EDTA, 150 mM NaCl, 10% glycerol, 1 mg/ml ovalbumin and 5 mM DTT, using 0.025 μCi per well $^3$H-Estradiol(NEN #NET517 at 118 Ci/mmol, 1 mCi/ml), 10 ng/well ERAlpha or ERbeta receptor (PanVera). Competing compounds are added at 10 different concentrations. Non-specific binding is determined in the presence of 1 μM of 17-B Estradiol. The binding reaction (140 μl) is incubated for 4 hours at room temperature, and 70 μl of cold DCC buffer is added to each reaction (DCC buffer contains per 50 ml of assay buffer, 0.75 g of charcoal (Sigma) and 0.25 g of dextran (Pharmacia)). Plates are mixed 8 minutes on an orbital shaker at 4° C. Plates are then centrifuged at 3,000 rpm at 4° C. for 10 minutes. An aliquot of 120 μl of the-mix is transferred to another 96-well, white flat bottom plate (Costar) and 175 μl of Wallac Optiphase "Hisafe 3" scintillation fluid is added to each well. Plates are sealed and shaken vigorously on an orbital shaker. After an incubation of 2.5 hrs, read plates in a Wallac Microbeta counter. The data is used to calculate an IC50 and % Inhibition at 10 μM. The $K_d$ for $^3$H-Estradiol is determined by saturation binding to ER alpha and ER beta receptors. The $IC_{50}$ values for compounds are converted to $K_i$ using Cheng-Prusoff equation and the $K_d$ determined by saturation binding assay.

Ishikawa Alkaline Phosphatase Assay

Ishikawa human endometrial tumor cells are maintained in MEM (minimum essential medium, with Earle's salts and L-Glutamine, Gibco BRL, Gaithersburg, Md.), supplemented with 10% fetal bovine serum (FBS) (V/V), (Gibco BRL). One day prior to assay, growth media is changed to assay medium, DMEM/F-12 (3:1) (Dulbecco's Modified Eagle Medium: Nutrient Mixture F-12, 3:1 Mixture, phenol red-free, Gibco BRL) supplemented with 5% dextran coated charcoal stripped fetal bovine serum (DCC-FBS) (Hyclone, Logen, Utah), L-Glutamine (2 mM), MEM sodium pyruvate (1 mM), HEPES (N-[2-hydroxyethyl]piperazine-N'-[2-ethanesulfonic acid] 2 mM) all from Gibco BRL). After an overnight incubation, ishikawa cells are rinsed with Dulbecco's Phosphate Buffered Saline (1×) (D-PBS) without $Ca^{+2}$ and $Mg^{+2}$ (Gibco BRL), and typsinized by a 3 minute incubation with 0.25% Trypsin/EDTA, phenol red-free (Gibco BRL). Cells are resuspended in assay medium and adjusted to 250,000 cells/ml. Approximately 25,000 cells in a 100 ul media are added to flat-bottom 96 wells microculture plates (Costar 3596) and incubated at 37° C. in a 5% $CO_2$ humidified incubator for 24 hours. The next day, serial dilutions of compounds are prepared in assay medium (at 6 times the final concentration in the assay). The assay is run in dual mode, agonist and antagonist modes. For the agonist mode, plates receive 25 μl/well of assay medium followed by 25 μl/well of diluted compounds (at 6× the final concentrations). For the antagonist mode, plates receive 25 μl/well of 6 nM $E_2$ (β-Estradiol, Sigma, St. Louis, Mo.) followed by 25 μl/well of diluted compounds (at 6× the final concentrations). After an additional 48-hour incubation at 37° C. in a 5% $CO_2$ humidified incubator, media is aspirated from wells and 100 μl fresh assay medium is added to each microculture. Serial dilutions of compounds are prepared and added to the cells as described above. After an additional 72 hour incubation at 37° C. in a 5% $CO_2$ humidified incubator, the assay is quenched by removing media and rinsing plates twice in Dulbecco's Phosphate Buffered Saline (1×) (D-PBS) (Gibco BRL). The plates are dried for 5 min and frozen at −70° C. for at least 1 hour. The plates are then removed from the freezer and allowed to thaw at room temperature. To each well, 100 μl of 1-Step™ PNPP (Pierce Chemical Company, Rockford, Ill.) is added. After a 20-minute incubation, plates are read on a spectophotometer at 405 nm. The data is fitted to a linear interpolation to derive EC50 (for agonist mode) or IC50 (for antagonist mode) values. For the agonist mode, a % efficacy for each compound is calculated versus the response to Tamoxifen. For the antagonist mode, a % efficacy for each compound is calculated versus E2 (1 nM) alone.

MCF-7 Proliferation Assay

MCF-7 breast adenocarcinoma cells (ATCC HTB 22) are maintained in MEM (minimal essential medium, phenol red-free, Gibco BRL) supplemented with 10% fetal bovine serum (FBS) (VN), L-glutamine (2 mM), sodium pyruvate (1 mM), HEPES ((N-[2-hydroxyethyl]piperazine-N'-[2-ethanesulfonic acid]) 10 mM}, non-essential amino acids (0.1 mM)and Penicillin Streptomycin(1×). Seven days prior to assay, MCF-7 cells are switched to assay media which is the same as maintenance medium except supplemented with 10% dextran-coated charcoal-stripped fetal bovine serum (DCC-FBS) assay medium in place of 10% FBS. MCF-7 cells are removed from flasks using 10× Trypsin EDTA (phenol red free, Gibco BRL) and diluted to 1× in (Ca++/Mg++ free HBSS (phenol red-free). Cells are adjusted to 80,000 cells/ml in assay medium. Approximately 8,000 cells (100 µl) are added to each well in 96 well Cytostar T scintillation plates (Amersham) and incubated at 37° C. in a 5% $CO_2$ humidified incubator for 24 hours to allow cell adherence and equilibration after transfer. Serial dilutions of drugs are prepared in assay medium at 4× the final desired concentration). A 50 µl aliquot of drug dilutions (at 4× the final assay concentration) is transferred to duplicate wells followed by 50 µl assay medium for the agonist mode or 50 µl of 40 pM of E2 for the antagonist mode to a final volume of 200 µl. For each of the agonist plates, a basal level (media) and a maximum stimulated level (with 1 µM E2) is determined. For each of the antagonist plates, a basal level (media) and a E2 (10 pM) alone control is determined. After an additional 48 hours at 37° C. in a 5% $CO_2$ humidified incubator, 20 µl of assay medium containing 0.01 µCi of $^{14}C$-thymidine (52 mCi/mmol, 50 µCi/ul, Amersham) is added to each well. The plates are incubated overnight in the same incubator and then counted on the Wallac Microbeta counter. The data is averaged to calculate an IC50 and % inhibition @1 µM for the antagonist mode. For the agonist mode, an EC50 and percent of maximum E2 stimulation and concentration of maximum stimulation is calculated.

dosing with a compound of formula (I) ("F-I") is initiated. 17α-ethynyl estradiol or F-I is given orally, unless otherwise stated, as a suspension in 1% carboxymethylcellulose or dissolved in 20% cyclodextrin. Animals are dosed daily for 4 days. Following the dosing regimen, animals are weighed and anasthetized with a ketamine: Xylazine (2:1, v:v) mixture and a blood sample is collected by cardiac puncture. The animals are then sacrificed by asphyxiation with $CO_2$, the uterus is removed through a midline incision, and a wet uterine weight is determined. 17α-ethynyl estradiol is obtained from Sigma Chemical Co., St. Louis, Mo.

Cardiovascular Disease/Hyperlipidemia

The blood samples from above are allowed to clot at room temperature for 2 hours, and serum is obtained following centrifugation for 10 minutes at 3000 rpm. Serum cholesterol is determined using a Boehringer Mannheim Diagnostics high performance cholesterol assay. Briefly the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay

The uteri from above are kept at 4° C. until time of enzymatic analysis. The uteri are then homogenized in 50 volumes of 50 mM Tris buffer (pH—8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosonophils in the uterus is an indication of estrogenic activity of a compound. The

TABLE

| Cmpnd (Ex. No.) | $K_i$ (ERα) | $K_i$ (ERβ) | IC50 (MCF7) | Ishikawa EC50 | Agonist % Eff | IC50 | % Eff |
|---|---|---|---|---|---|---|---|
| 1 | A* | A | B† | 22.9 | 18 | | 18 |
| 2 | A | A | B | | −5 | | 28 |
| 3a | 87.8 | 1155.1 | 989 | 239.21 | 29 | | 17 |
| 4 | 28.9 | 376.3 | 618 | 84.77 | 44 | 667 | 47 |
| 7 | 0.4 | 4.4 | 477 | 219.09 | 28 | | 17 |
| 8 | 1.3 | 4.1 | 532 | 28.38 | 31 | 716 | 63 |
| 10 | 1.1 | 4.9 | 68 | 33.5 | 18 | 553 | 40 |
| 12a | 0.6 | 5.9 | 385 | 142.41 | 29 | 892 | 31 |

*A means < 50% binding at 10 microMolar
†B means < 50% inhibition at 1 micromolar
a signifies the trifluoroacetic acid (TFA) salt General Rat Preparation Procedure Seventy-five day old (unless otherwise indicated) female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room was 12 hours light and 12 hours dark.

Dosing Regimen Tissue Collection: After a one week acclimation period (therefore, two weeks post-OVX) daily maximal velocity of a 15 second interval is determined over the initial, linear portion of the reaction curve.

Inhibition of Bone Loss (Osteoporosis) Test Procedure

Following the general preparation procedure described above, the rats are treated daily for thirty-five days (6 rats per treatment group) and sacrificed by carbon dioxide asphyxiation on the 36th day. The thirty-five day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitalized X-rays generated and analyzed by an image analysis program (NIH image) at the distal metaphysis. The proximal aspect of the tibiae from these animals are also scanned by quantitative computed tomography. In accordance with the above procedures, F-I or ethynyl estradiol ($EE_2$) in 20% hydroxypropyl β-cyclodextrin are orally administered to test animals. F-I is also useful in combination with estrogen or progestin.

Uterine Fibrosis Test Procedures

Test 1: Between 3 and 20 women having uterine fibrosis are administered F-I. The amount of compound administered is from 0.1 to 1000 mg/day, and the period of administration is 3 months. The women are observed during the period of administration, and up to 3 months after discontinuance of administration, for effects on uterine fibrosis.

Test 2: The same procedure is used as in Test 1, except the period of administration is 6 months.

Test 3: The same procedure is used as in Test 1, except the period of administration is 1 year.

Test 4: Prolonged estrogen stimulation is used to induce leiomyomata in sexually mature female guinea pigs. Animals are dosed with estradiol 3–5 times per week by injection for 2–4 months or until tumors arise. Treatment consisting of F-I or vehicle is administered daily for 3–16 weeks and then animals are sacrificed and the uteri harvested and analyzed for tumor regression.

Test 5: Tissue from human leiomyomas are implanted into the peritoneal cavity and/or uterine myometrium of sexually mature, castrated, female, nude mice. Exogenous estrogen is supplied to induce growth of the explanted tissue. In some cases, the harvested tumor cells are cultured in vitro prior to implantation. Treatment consisting of F-I or vehicle is supplied by gastric lavage on a daily basis for 3–16 weeks and implants are removed and measured for growth or regression. At the time of sacrifice, the uteri are harvested to assess the status of the organ.

Test 6: Tissue from human uterine fibroid tumors is harvested and maintained, in vitro, as primary non-transformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, F-I, and vehicle. Levels of steroid hormone receptors are assessed weekly to determine whether important cell characteristics are maintained in vitro. Tissue from 5–25 patients is utilized.

Test 7: F-I's ability to inhibit estrogen-stimulated proliferation of leiomyoma-derived ELT cell lines is measured substantially as described in Fuchs-Young, et al., "Inhibition of Estrogen-Stimulated Growth of Uterine Leiomyomas by Selective Estrogen Receptor Modulators", Mol. Car., 17(3): 151–159 (1996), the teachings of which are herein incorporated by reference.

Endometriosis Test Procedures

Test 1: Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed. On the day following surgery, animals in Groups 1 and 2 receive intraperitoneal injections of water for 14 days whereas animals in Group 3 receive intraperitoneal injections of 1.0 mg of F-I per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Test 2: Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. Approximately 50 days following surgery, animals assigned to Group 1 receive intraperitoneal injections of water for 21 days whereas animals in Group 2 receive intraperitoneal injections of 1.0 mg of F-I per kilogram of body weight for the same duration. Following 21 days of treatment, each female is sacrificed and the endometrial explants and adrenals are removed and weighed. The explants are measured as an indication of growth. Estrous cycles are monitored.

Test 3: Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

Test 4: Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of F-I supplied by gastric lavage on a daily basis for 3–16 weeks, and implants are removed and measured for growth or regression. At the time of sacrifice, the uteri are harvested to assess the status of the intact endometrium.

Test 5: Tissue from human endometrial lesions is harvested and maintained in vitro as primary non-transformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, F-I, and vehicle. Levels of steroid hormone receptors are assessed weekly to determine whether important cell characteristics are maintained in vitro. Tissue from 5–25 patients is utilized.

Use of Formula (I) Compound in Conjunction with Estrogen

Peri- and post-menopausal women often undergo hormone replacement therapy (HRT) to combat negative consequences associated with the drop in circulating endogenous estrogen, e.g., to treat hot flashes. However, HRT has been associated with increased risks of certain cancers including uterine and breast cancer. F-I may be employed in conjunction with HRT to inhibit these risks.

Prevention of Breast Cancer

This invention also relates to the administration of F-I to a recipient who is at risk of developing de novo breast cancer. The term "de novo", as used herein, means the lack of transformation or metamorphosis of normal breast cells to cancerous or malignant cells in the first instance. Such a transformation may occur in stages in the same or daughter cells via an evolutionary process or may occur in a single, pivotal event. This de novo process is in contrast to the metastasis, colonization, or spreading of already transformed or malignant cells from the primary tumor site to new locations.

A person who is at no particular risk of developing breast cancer is one who may develop de novo breast cancer, has no evidence or suspicion of the potential of the disease above normal risk, and who has never had a diagnosis of having the disease. The greatest risk factor contributing to the development of breast carcinoma is a personal history of suffering from the disease, or an earlier occurrence of the disease, even if it is in remission with no evidence of its presence. Another risk factor is family history of the disease.

Induction of mammary tumors in rats by administration of the carcinogen N-nitroso-N-methylurea is a well-accepted animal model for the study of breast cancer and has been found suitable for analyzing the effect of chemopreventive agents.

In two separate studies, 55-day old female Sprague-Dawley rats are given an intravenous (Study 1) or intraperitoneal (Study 2) dose of 50 mg of N-nitroso-N-methylurea per kilogram of body weight one week prior to feeding ad libitum a diet into which varying amounts of F-1, (Z)-2-[4-(1,2-diphenyl-1-butenyl)phenoxy]-N,N-dimethylethanamine base (tamoxifen base), or control are blended.

In Study 1, the dietary doses of 60 mg/kg of diet and 20 mg/kg of diet translates into roughly comparable doses of 3 and 1 mg/kg of body weight for the test animals.

In Study 2, the dietary doses of 20, 6, 2, and 0.6 mg/kg of diet translates roughly into comparable doses of 1, 0.3, 0.1 and 0.03 mg/kg of body weight for the test animals.

Rats are observed for evidence of toxicity and are weighed and palpated for tumor formation once a week. The animals are sacrificed after thirteen weeks (Study 1) or eighteen weeks (Study 2) and tumors are confirmed and weighed at autopsy.

Therapeutic Methods of Use and Dosages

The present invention also provides a method of inhibiting a disease associated with estrogen deprivation and a method for inhibiting a disease associated with an aberrant physiological response to endogenous estrogen which comprises the aforementioned method using compounds of Formula I and optionally comprises administering to a patient an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra indicates that the combination treatments are useful for alleviating the symptoms of post-menopausal symptoms in women.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin®, and norethylnodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "patient" refers to a warm-blooded animal or mammal which is in need of inhibiting a disease associated with estrogen deprivation or in need of inhibiting a disease associated with an aberrant physiological response to endogenous estrogen. It is understood that guinea pigs, dogs, cats, rats, mice, hamsters, and primates, including humans, are examples of patients within the scope of the meaning of the term. Preferred patients include humans. Most preferred patients include postmenopausal female humans.

As used herein, the term "inhibit" is defined to include its generally accepted meaning which includes preventing, prohibiting, restraining, and slowing, stopping or reversing progression, or severity, and holding in check and/or treating existing characteristics. The present method includes both medical therapeutic and/or prophylactic treatment, as appropriate.

The term "estrogen deprivation" is meant to imply the condition where the optimal level of estrogen is absent. This level varies from one tissue to another depending on the function of the tissue. Thus, in some cases, estrogen deprivation may be the total absence of estrogen, whereas in other cases, deprivation may involve estrogen levels which are too low for proper tissue function. In human women, the two most common causes of estrogen deprivation are menopause and ovariectomy, although other conditions can be causative. Estrogen deprivation can lead to conditions including osteoporosis and cardiovascular effects such as hyperlipidemia, proliferation of aortal smooth muscle cells (restenosis), decrease in nitric oxide production (hypertension) and decrease in production of the enzyme PAI-1 (Plasminogen Activator Inhibitor-1), i.e. thrombosis.

Reduction or amelioration of other pathologies associated with menopause such as urinary incontinence, vaginal dryness, increase in the incidence of auto-immune disease, and loss of skin tone, may also be achieved by administering compounds of Formula I.

In addition to their usefulness in treating conditions associated with estrogen deprivation following menopause, the compounds of the present invention are also useful in the treatment of disease states associated with inappropriate response to endogenous estrogen in tissues both prior to and subsequent to menopause.

One example of a pathological condition associated with abnormal cellular responses to endogenous estrogen in tissues is estrogen dependent breast cancer. Estrogen dependent breast tumor cells proliferate in the presence of estrogen and the treatment of this disease has been to stop all action of estrogen on these cells.

Another estrogen dependent pathology is uterine fibrosis (uterine fibroid disease). Essentially, uterine fibrosis is a condition where there is a deposition of fibroid tissue on the wall of the uterus. This condition is a cause of dysmenorrhea and infertility in women. The exact cause of this condition is poorly understood but evidence suggests that it is an inappropriate response of fibroid tissue to estrogen. The most common treatment of uterine fibrosis involves surgical procedures both costly and sometimes a source of complications such as the formation of abdominal adhesions and infections.

Yet another disease in this category is endometriosis, a condition of severe dysmenorrhea, which is accompanied by severe pain, bleeding into the endometrial masses or peritoneal cavity and often leads to infertility. The cause of the symptoms of this condition appear to be ectopic endometrial growths located in inappropriate tissues which respond inappropriately to hormonal control.

As used herein, the term "therapeutically effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose for human use will contain a nontoxic dosage level of from about 1 mg to about 600 mg/day of a compound of the present invention. Preferred daily doses generally will be from about 15 mg to about 300 mg/day. Most preferred doses range may constitute 10 mg, 20 mg, 30 mg, 40 mg, 50 mg, 60 mg, 70 mg, 80 mg, 90 mg, and 100 mg, administered once to three times per day.

The compounds of this invention can be administered by a variety of routes including oral, rectal, transdermal, subucutaneus, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, alone or in combination with a pharmaceutical agent of the present invention, generally will be administered in a convenient formulation.

I claim:
1. A compound of the formula

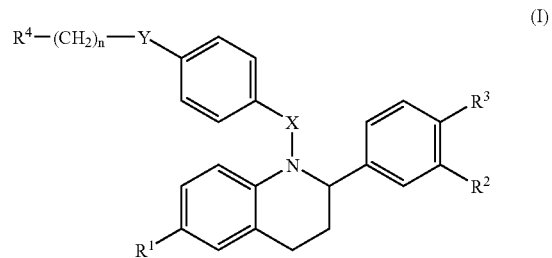

(I)

wherein
R$^1$ is —H, —OH, —O(C$_1$–C$_4$ alkyl), —OCOC$_6$H$_5$, —OCO(C$_1$–C$_6$ alkyl), or —OSO$_2$(C$_2$–C$_6$ alkyl);
R$^2$ and R$^3$ are each independently —H, —OH, —O(C$_1$–C$_4$ alkyl), —OCOC$_6$H$_5$, —OCO(C$_1$–C$_6$ alkyl), —OSO$_2$(C$_2$–C$_6$ alkyl) or halo:
R$^4$ is 1-piperidinyl, 1-pyrrolidinyl, methyl-1-pyrrolidinyl, dimethyl-1-pyrrolidinyl, 4-morpholino, dimethylainino, diethylamino, diisopropylamino, or 1-hexamethyleneimino;
n is 1, 2 or 3;
X is —C(O)— or —CH$_2$—; and
Y is —O—, —S—, —NH—, —NMe-, or —CH$_2$—; or an enantiomer, or a pharmaceutically acceptable salt, thereof.

2. A compound according to claim 1 wherein X is —CH$_2$—, or a pharmaceutically acceptable salt thereof.

3. A compound according to claim 2 wherein Y is —O—.

4. A compound according to claim 3 wherein n is 2, or a pharmaceutically acceptable salt thereof.

5. A compound according to claim 4 wherein R$^1$ is —OH, or a pharmaceutically acceptable salt thereof.

6. A compound according to claim 5 wherein R$^4$ is 1-piperidinyl, or a pharmaceutically acceptable salt thereof.

7. A compound according to claim 3 wherein one of R$^2$ or R$^3$ is —OH, or a pharmaceutically acceptable salt thereof.

8. A compound according to claim 5 wherein one of $R^2$ or $R^3$ is —OH, or a pharmaceutically acceptable salt thereof.

9. A compound according to claim 6 wherein one of $R^2$ and $R^3$ is —H or a pharmaceutically acceptable salt thereof.

10. A compound according to claim 1 wherein X is —C(O)—, or a pharmaceutically acceptable salt thereof.

11. A compound according to claim 10 wherein Y is —O—.

12. A compound according to claim 11 wherein n is 2, or a pharmaceutically acceptable salt thereof.

13. A compound according to claim 12 wherein $R^1$ is —OH, or a pharmaceutically acceptable salt thereof.

14. A compound according to claim 13 wherein $R^4$ is 1-piperidinyl, or a pharmaceutically acceptable salt thereof.

15. A compound according to claim 11 wherein one of $R^2$ or $R^3$ is —OH, or a pharmaceutically acceptable salt thereof.

16. A compound according to claim 13 wherein one of $R^2$ or $R^3$ is —OH, or a pharmaceutically acceptable salt thereof.

17. A compound according to claim 14 wherein one of $R^2$ and $R^3$ is —H or a pharmaceutically acceptable salt thereof.

18. A compound according to claim 1 selected from the group consisting of:
[6-methoxy-2-(4-methoxyphenyl)-3,4-dihydro-2H-quinolin-1-yl]-[4(  2-piperidin-1-yl-ethoxy)phenyl]methanone;
(6-methoxy-2-phenyl-3,4-dihydro-2H-quinolin-1-yl]-[4-(2-piperidin-1-yl-ethoxy)phenyl]methanone;
[6-hydroxy-2-(4-hydroxyphenyl)-3,4-dihydro-2H-quinolin-1-yl]-[4-2-piperidin-1-yl-ethoxy)phenyl]methanone;
(6-hydroxy-2-phenyl-3,4-dihydro-2H-quinolin-1-yl)-[4-(2-piperidin-1-yl-ethoxy)phenyl]methanone;
6-methoxy-2-phenyl-1-[4-(2-piperidin-1-yl-ethoxy)benzyl]-1,2,3,4-tetrahydroquinoline;
6-methoxy-2-phenyl-1-[4-(2-piperidin-1-yl-ethoxy)benzyl]-1,2,3,4-tetrahydroquinoline;
2-(4-hydroxyphenyl)-1-[4-(2-piperidin-1-yl-ethoxy)benzyl]-1,2,3,4-tetrahydroquinolin-6-ol;
2-phenyl-1-[4-(2-piperidin-1-yl-ethoxy)benzyl]-1,2,3,4-tetrahydroquinolin-6ol;
6-methoxy-2-(4-methoxyphenyl)-1-[4-(2-pyrrolidin-1-yl-ethoxy)benzyl]-1,2,3,4-tetrahydroquinoline;
2-(4-hydroxyphenyl)-1-[4-(2-piperidin-1-yl-ethoxy)benzyl]-1,2,3,4-tetrahydroquinolin-6-ol;
6-methoxy-2-(3-methoxyphenyl)-1-[4-(2-piperidin-1-yl-ethoxy)-benzyl]-1,2,3,4-tetrahydro-quinoline; and
2-(3-hydroxyphenyl)-1-[4-(2-piperidin-1-yl-ethoxy)-benzyl]-1,2,3,4-tetrahydro-quinolin-6-ol; or a pharmaceutically acceptable salt thereof.

19. A compound according to claim 1 wherein said compound is 2-(4-hydroxyphenyl)-1-[4-(2-piperidin-1-yl-ethoxy)benzyl]-1,2,3,4-tetrahydroquinolin-6-ol, or a pharmaceutically acceptable salt thereof.

20. A compound according to claim 1 wherein said compound is 2-(3-hydroxyphenyl)-1-[4-(2-piperidin-1-yl-ethoxy)-benzyl]-1,2,3,4-tetrahydro-quinolin-6-ol, or a pharmaceutically acceptable salt thereof.

21. A pharmaceutical composition comprising a compound according to claim 1, or a pharmaceutically acceptable salt thereof, and, optionally, an effective amount of estrogen or progestin, in combination with a pharmaceutically acceptable salt, diluent, or excipient.

22. A method for treating osteoporosis and cardiovascular diseases caused by estrogen deprivation "a method for" selected from the group consisting of hyperlipidemia, proliferation of aortal smooth muscle cells, hypertension and thrombosis "the group consisting of" "comprising administering" comprising administering to a patient in need thereof a therapeutically effective amount of a compound of the formula

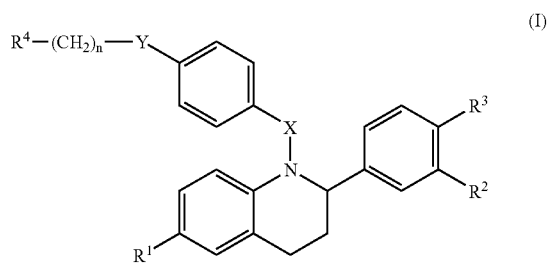

wherein
$R^1$ is —H, —OH, —O($C_1$–$C_4$ alkyl), —OCO$C_6H_5$, —OCO($C_1$–$C_6$ alkyl), or —OSO$_2$($C_2$–$C_6$ alkyl);
$R^2$ and $R^3$ are each independently —H, —OH, —O($C_1$–$C_4$ alkyl), —OCO$C_6H_5$, —OCO($C_1$–$C_6$ alkyl), —OSO$_2$($C_2$–$C_6$ alkyl) or halo;
$R^4$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;
n is 1,2 or 3;
X is —C(O)— or —CH$_2$—; and
Y is —O—, —S—, —NH—, —NMe-, or —CH$_2$—; or a pharmaceutically acceptable salt thereof.

23. A method according to claim 22 wherein said patient is a human.

24. A method according to claim 23 wherein the human is a postmenopausal female.

25. A method according to claim 22 wherein said disease associated is osteoporosis.

26. A method according to claim 22 wherein said disease selected from the group consisting of hyperlipidemia, proliferation of aortal smooth muscle cells, hypertension and thrombosis "cardiovascular disease" is cardiovascular disease.

27. A method for treating a disease selected from the group consisting of estrogen dependent breast cancer, endometriosis, and uterine fibrosis comprising administering to a patient in need thereof a therapeutically effective amount of a compound of the formula

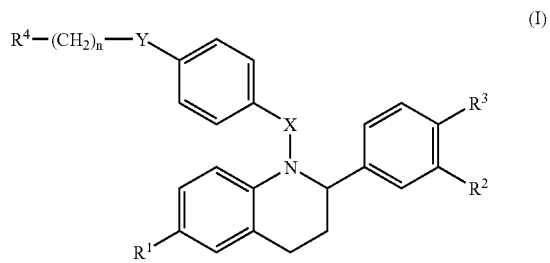

wherein
$R^1$ is —H, —OH, —O($C_1$–$C_4$ alkyl), —OCO$C_6H_5$, —OCO($C_1$–$C_6$ alkyl), or —OSO$_2$($C_2$–$C_6$ alkyl);
$R^2$ and $R^3$ are each independently —H, —OH, —O($C_1$–$C_4$ alkyl), —OCO$C_6H_5$, —OCO($C_1$–$C_6$ alkyl), —OSO$_2$($C_2$–$C_6$ alkyl) or halo;

R⁴ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;

n is 1,2 or 3;

X is —C(O)— or —CH₂—; and

Y is —O—, —S—, —NH—, —NMe-, or —CH₂—; or a pharmaceutically acceptable salt thereof.

28. A method according to claim 27 wherein said patient is a human.

29. A method according to claim 28 wherein the human is a postmenopausal female.

30. A method according to claim 27 wherein the disease is estrogen dependent breast cancer.

31. A method according to claim 27 wherein the disease is endometriosis.

32. A method according to claim 27 wherein the disease is uterine fibrosis.

* * * * *